US008374888B2

(12) United States Patent
Earles et al.

(10) Patent No.: US 8,374,888 B2
(45) Date of Patent: Feb. 12, 2013

(54) BEHAVIOR MONITORING AND REINFORCEMENT SYSTEM AND METHOD

(75) Inventors: Alison C. Earles, Atlanta, GA (US); Jeffrey Pawlan, San Jose, CA (US)

(73) Assignee: Ace Ideas, LLC, Atlanta, GA (US)

( * ) Notice: Subject to any disclaimer, the term of this patent is extended or adjusted under 35 U.S.C. 154(b) by 1519 days.

(21) Appl. No.: 11/588,307

(22) Filed: Oct. 27, 2006

(65) Prior Publication Data

US 2007/0100595 A1    May 3, 2007

(51) Int. Cl.
G06Q 50/00 (2012.01)
G06Q 10/00 (2012.01)
(52) U.S. Cl. ................................. 705/2; 705/3
(58) Field of Classification Search .................... 705/11, 705/2
See application file for complete search history.

(56) References Cited

U.S. PATENT DOCUMENTS

| | | | |
|---|---|---|---|
| 4,592,018 A | 5/1986 | Wiegman | |
| 5,301,105 A | 4/1994 | Cummings, Jr. | |
| 5,692,501 A | 12/1997 | Minturn | |
| 5,722,418 A | 3/1998 | Bro | |
| 5,827,180 A | 10/1998 | Goodman | |
| 5,832,448 A * | 11/1998 | Brown | 705/2 |
| 5,933,136 A * | 8/1999 | Brown | 715/741 |
| 5,937,387 A | 8/1999 | Summerell et al. | |
| 6,039,688 A | 3/2000 | Douglas et al. | |
| 6,512,456 B1 | 1/2003 | Taylor, Jr. | |
| 6,549,893 B1 | 4/2003 | Lannert et al. | |
| 6,605,038 B1 | 8/2003 | Teller et al. | |
| 6,689,057 B1 | 2/2004 | Shinsel et al. | |
| 6,699,188 B2 | 3/2004 | Wessel | |
| 6,705,972 B1 | 3/2004 | Takano et al. | |
| 6,798,898 B1 | 9/2004 | Fedorovskaya et al. | |
| 6,847,969 B1 | 1/2005 | Mathai et al. | |
| 6,850,890 B1 | 2/2005 | Roff | |
| 6,915,271 B1 | 7/2005 | Meyer et al. | |
| 6,925,441 B1 | 8/2005 | Jones, III et al. | |
| 6,961,562 B2 | 11/2005 | Ross | |
| 7,024,369 B1 | 4/2006 | Brown et al. | |
| 7,060,006 B1 | 6/2006 | Watterson et al. | |
| 7,064,681 B2 | 6/2006 | Horstemeyer | |
| 7,070,562 B2 | 7/2006 | Bardy | |
| 7,074,168 B1 | 7/2006 | Farnes et al. | |
| 7,091,865 B2 | 8/2006 | Cuddihy et al. | |
| 7,092,846 B2 | 8/2006 | Vock et al. | |
| 8,027,822 B2 | 9/2011 | Turgiss et al. | |
| 2003/0135391 A1 | 7/2003 | Edmundson et al. | |
| 2004/0010420 A1 | 1/2004 | Rooks | |
| 2004/0131997 A1 | 7/2004 | McGuire et al. | |

(Continued)

OTHER PUBLICATIONS

Guiffrida, Should We Pay the Patient? Review of Financial Incentives to Enhance Patient Compliance, BMJ: British Medical Journal, vol. 315, No. 7110 (Sep. 20, 1997), pp. 703-707.*

(Continued)

*Primary Examiner* — Dilek B Cobanoglu
*Assistant Examiner* — Ken Nguyen
(74) *Attorney, Agent, or Firm* — Edell, Shapiro & Finnan, LLC

(57) ABSTRACT

A system, method and computer software that provides for a computer implemented system and method for comprehensive reinforcement of human behavior by capturing environmental information for participants and reinforcing their daily choices in their environments. Unique applications of technology are used to record, reinforce and document the desired behavior activities of participants in order to track, promote, encourage and further reward the desired behavior.

28 Claims, 14 Drawing Sheets

U.S. PATENT DOCUMENTS

| | | | |
|---|---|---|---|
| 2004/0210458 A1 | 10/2004 | Evans et al. | |
| 2005/0015281 A1 | 1/2005 | Clark et al. | |
| 2005/0075908 A1 | 4/2005 | Stevens | |
| 2005/0228692 A1 | 10/2005 | Hodgdon | |
| 2005/0234742 A1 | 10/2005 | Hodgdon | |
| 2005/0240438 A1 | 10/2005 | Day | |
| 2006/0003305 A1 | 1/2006 | Kelmar | |
| 2006/0026036 A1 | 2/2006 | Mahmood | |
| 2006/0031102 A1 | 2/2006 | Teller et al. | |
| 2006/0100897 A1 | 5/2006 | Halloran, Jr. et al. | |
| 2006/0122474 A1 | 6/2006 | Teller et al. | |
| 2006/0136258 A1 | 6/2006 | Horn et al. | |
| 2006/0143645 A1 | 6/2006 | Vock et al. | |
| 2006/0218011 A1* | 9/2006 | Walker et al. | 705/3 |

OTHER PUBLICATIONS

Kahn, The effectiveness of interventions to increase physical activity, Task Force on Community Preventive Services, American Journal of Prevention Medicine. Vol22 No. 4S, pp. 73-107, 2002.*

"Agreement with Health Insurer PruHealth", ADDleisure Plc., Jun. 5, 2006.

Rick Redding. "Sweating for Dollars", www.kioskcom.com, Mar. 23, 2006.

"Virgin Life Care Launches in SA". Trojan Horse on behalf of Virgin Life Care, www.health24.com, Feb. 2006.

Travis E. Poling. "S.A. a Testing Ground for Effort to Get Workers in Shape", Feb. 8, 2006.

Greg Levine. "No PR Stunt: Branson's Virgin to 'Liven' Up Health Care", May 6, 2005.

Margie Manning. "Branson Looks to Add 'Sexy' Edge to Health Insurance Market". Date unknown.

"Virgin Life Care HealthZone Kiosk Wins Awards; IBM Provides Services, Hardware", Market Wire News, Boston, MA, Apr. 27, 2006.

W. Scott Bailey. "Virgin, Spectrum, Humana Rolling Out Program in S.A.", San Antonio Business Journal, Jan. 6, 2006.

"Three Simple Steps to Vitality". Discovery Vitality literature.

Brent Melville. Pulse Member Magazine, Jun. 2004.

* cited by examiner

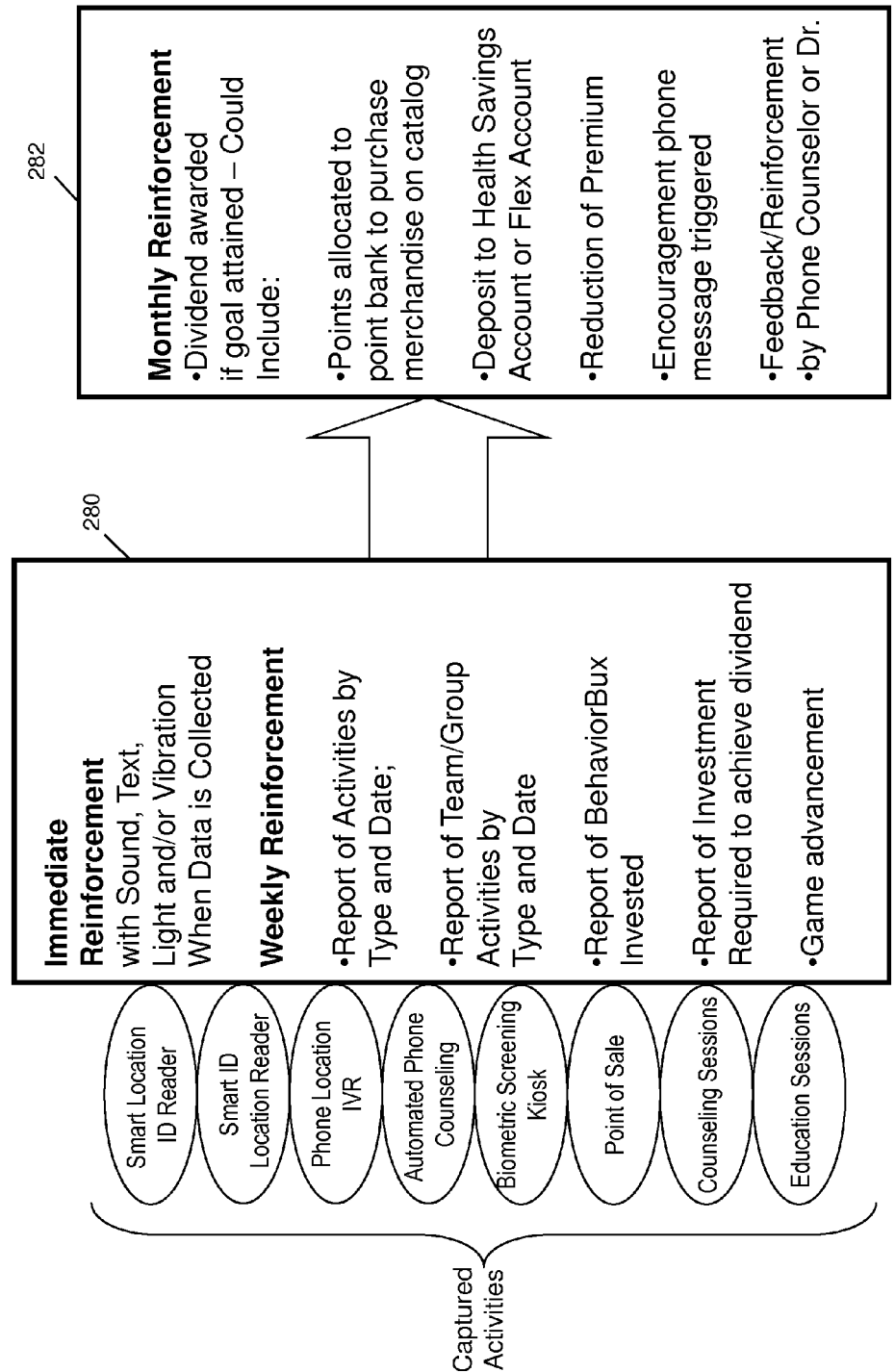

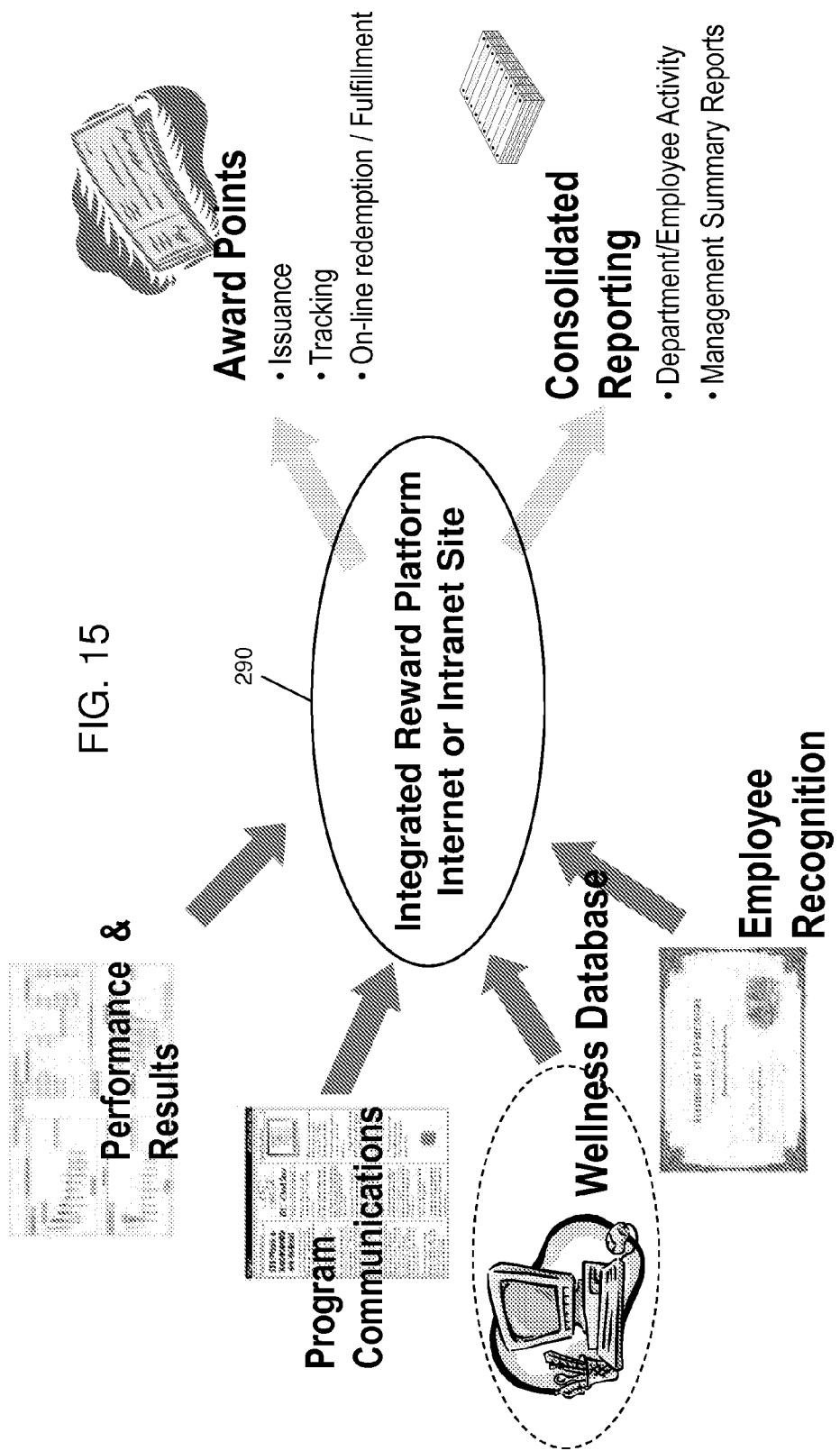

BEHAVIOR MONITORING AND REINFORCEMENT SYSTEM AND METHOD

BACKGROUND OF THE INVENTION

The present invention relates to systems and methods for encouraging and tracking improvements in human behaviors, including but not limited to, health or wellness.

Conventional healthcare and insurance databases concentrate on their members' use of healthcare services and orders for covered prescriptions. The members have little incentive to change their lifestyle or unhealthy habits since no benefits, price reductions, increased salary, or other incentives are offered for making healthy choices, which benefit not only the individual, but also the employer, the insurance company, and all other employees through reduced health care and insurance costs.

SUMMARY OF THE INVENTION

Accordingly, it is one goal of the present invention to provide an objective and documentable means of rewarding the good behaviors of individuals in the context of a behavior investment system. One example of such a behavior investment system is one that tracks, promotes and rewards health promoting behaviors and proven improvements in the health of participating members.

According to one embodiment, the system, method and computer software according to the invention provides for unique applications of technology to record and document the desired behavior activities of participants, and it also provides a degree of confidence and security that the participants honestly reported their activities.

Briefly, a computer implemented system and method are provided for comprehensive reinforcement of human behavior by capturing environmental information for participants and reinforcing their daily choices in their environments. The system and method involves storing information to enroll a plurality of individuals such that the individuals become participants (also called investors) in a comprehensive behavior reinforcement plan established by a sponsor entity. The comprehensive behavior reinforcement plan is designed to encourage one or more desired behaviors for the participants. The behavior reinforcement plan is also referred to herein as a behavior investment plan because participants receive investment credit for activities related to the desired behavior. Baseline data or measurements related to the one or more desired behaviors or its/their impact on the one or more desired behaviors for each participant is captured and store. Depending on the specific application of the behavior investment program, one or more handicapping (or adjustment) factors for a participant may be computed based on the baseline data or measurements that might affect the participant's ability (or speed of progress) to achieve desired behavior goals. On an ongoing basis, activity data is captured that represents participant activities that are relevant to the one or more desired behaviors for each participant. Based on the captured activity data, performance measurement data is computed for each participant that represents a measure of how the participant is progressing towards achievement of one or more desired behaviors. The performance measurement data for a particular participant may then be compared with respect to one or more other participants using the handicapping factors for the particular participant and the one or more other participants. The performance measurement data for a participant may also be presented to that corresponding participant. According to still a further aspect of the invention, communications may be made to a participant at the time that activity data is collected from a participant, where such communications are designed to reinforce the participant's progress towards, and achievement, of the one or more desired behaviors.

BRIEF DESCRIPTION OF THE DRAWINGS

FIG. 14 is a flow chart depicting different levels of delivering reinforcement messages to investors according to an embodiment of the invention.

FIG. 15 is a block diagram depicting an integrated reward platform that may be implemented as an Internet or intranet web side according to an embodiment of the invention.

DETAILED DESCRIPTION OF THE INVENTION

Figure 1:
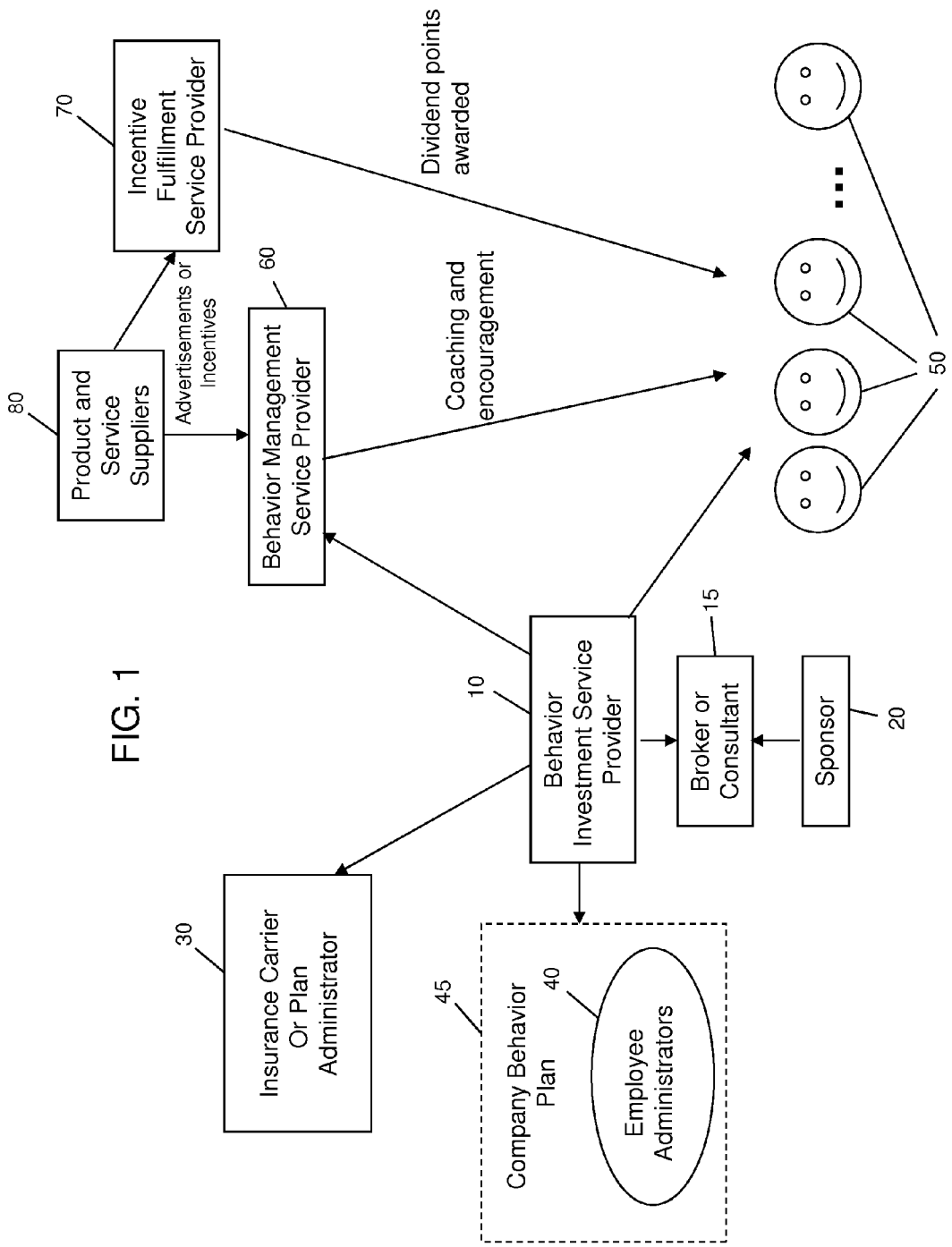
FIG. 1 is a block diagram showing the various entities that may have a role in a behavior investment program provided by the system and methods according to embodiments of the present invention.

Reference is made first to FIG. 1, where various entities are shown that have a role in a behavior investment program or plan. The behavior investment program is designed and managed by a behavior investment service provider 10 on behalf of a sponsor 20 who may be introduced to the behavior investment service provider 10 by a broker or consultant 15. One example of a behavior investment program or plan is a health benefits plan and the health benefits plan is used throughout this description as one example of a particular type of behavior investment program. It should be understood that there are numerous applications of the system and methods (examples of which are provided hereinafter) described herein other than health benefit plans.

Associated with the behavior investment plan there may be an insurance carrier or plan administrator 30. For example, in the case of a health benefits plan, the insurance carrier is a health insurance provider. If the sponsor 20 is an employer, then the behavior investment service provider 10 communicates with employee administrators 40 that are responsible for deployment of the behavior plan shown at 45. The participants in the plan are shown at reference numeral 50. The term participant is also used herein interchangeably with the term "investor" because the plan participants are investing in improving or maintaining one or more desired behaviors as part of the plan. The value of the desired behavior may be expressed in terms of investment as a certain number of so-called "BehaviorBux™". Moreover, participants may be awarded investment credit for engaging in an activity related to a desired behavior with another participant. Investment credit for engaging another participant in a desired behavior related activity is given the term "BuddyBux™" hereinafter. Furthermore, investment credit awarded in health behavior investment program may be referred to herein as "HealthBux™". The terms BehaviorBux™, BuddyBux™ and HealthBux™ are trademarks of Ace Consulting, LLC, and their usage throughout this description and the accompanying figures in no way relinquishes any rights in those terms as trademarks of Ace Consulting, LLC.

As a result of their behavior improvement or maintenance improvement, the participants may actually receive a financial benefit in various forms, including but not limited to, reduced health insurance premiums and products or services earned as a result of achieving certain improvement or maintenance goals.

The behavior investment service provider 10 may engage the services of a behavior management service provider 60. The behavior management service provider 60 may provide consultation services to investors 50 in order to help investors improve one or more behaviors and to provide related encouragement.

An incentive fulfillment service provider 70 may also be involved to keep track of incentive awards built up by investors 50 by achieving certain goals or meeting certain challenges as part of the behavior investment plan. The incentive awards may be measured in so-called dividend "points" that have financial value, and which can be redeemed by an investor with one or more product and service suppliers shown at 80.

Figure 2:
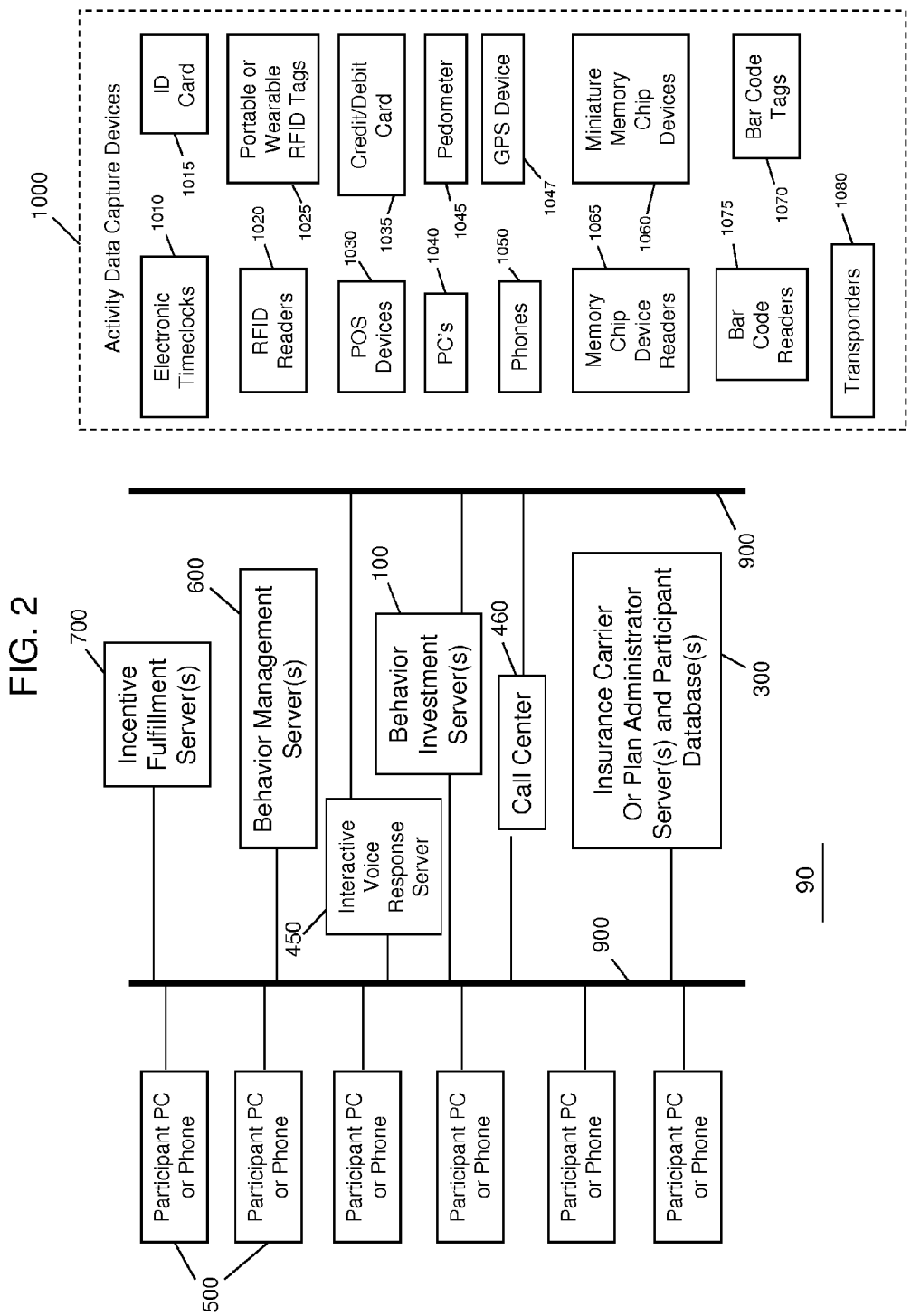
FIG. 2 is a block diagram of a behavior investment system according to an embodiment of the present invention.

Turning to FIG. 2, a block diagram of a behavior investment system 90 according to one embodiment is described. The behavior investment system 90 is a computer-implemented system and may be implemented on computer server based platform, or a stand-alone computing platform depending on the particular application and scalability required. The behavior investment system 90 provides for comprehensive reinforcement of human behavior by capturing environmental information about participants and reinforcing their daily choices in their environments. At the heart of the system 90 is a behavior investment server 100 that performs various data management, reporting and other functions to implement the behavior investment plan or program. There may be additional servers that store activity data before transmission or downloads of the activity data to the behavior investment server 100. For example, the manufacturer of an activity monitor or biometric screening monitor may store data on their servers before the data is transmitted or downloaded to the behavior investment server. If there is an insurance carrier or plan administrator for the behavior investment plan, then there may be an associated insurance carrier or plan administrator server and participant database shown at 300. Similarly, there may be a behavior management server 600 associated with the behavior management service provider 60 and an incentive fulfillment server 700 associated with the incentive fulfillment service provider 70. Communication and exchange of data between these servers may be achieved through a network 900 (e.g., Internet) that may comprise local (wired and wireless) area networks, wide area (wired and wireless) and wired and wireless telephone networks. Similarly, a participant or investor may communicate and exchange data with any of these servers via a participant PC or phone 500 connected to the network 900. There may also be an interactive voice response server 450 to provide for telephone based voice interactivity between participants and the behavior investment server 100, and between persons at the third party service providers as well for purpose of activity data capture, incentive fulfillment, etc. Similarly, there may be a call center 460 that provides live interactive telephone contact with participants and/or individuals associated with activity data capture, incentive fulfillment, etc.

In addition, there are one or more activity data capture devices shown at 1000 for purposes of capturing data for investor activities that are related to the behavior investment plan. Non-limiting examples of these data capture devices are shown in FIG. 2, but it should be understood that other devices heretofore known or hereinafter developed may also be used to register and track certain investor activities that are relevant to a behavior investment plan. Certain component or elements of the activity data capture devices may be deployed at variations locations within a building or across a campus of buildings associated with a work environment, at third party locations such as wellness clinics, health clubs, pharmacies, participants' homes, etc. For example, in one embodiment, there may be an electronic time clock or security card reader 1010 that reads data from an ID card 1015 to indicate that a person associated with that ID card is present at a particular place/location. There may be radio frequency identifier (RFID) readers 1020 deployed at various locations that read portable or wearable RFID tags 10250 of a participant. There may be point of sale (POS) terminal devices 1030 that accumulate information associated with a sales transaction made by a participant's credit/debit card 1035. A standard person computer (PC) 1040 may be used to allow a user to input and upload activity related data, or to interface with a peripheral device such as an electronic pedometer 1045 or GPS device 1047. The electronic pedometer 1045 can store data indicating the distance that a person may have traveled over a period of time, and likewise the GPS device 1047 may store similar information, albeit generated by different means. A standard landline telephone or mobile wireless telephone 1050 may be used to register a certain type of behavior related activity.

Still other types of activity data capture devices include miniature memory chip devices 1060, known commercially as an Ibutton™ made and distributed by Dallas Semiconductor, Inc. These devices are very small and capable of being deployed as portable or wearable person identifier devices. The data which these devices store may be read by dedicated memory chip device readers 1065 or in some cases by a standard PC as well. Other forms of determining that an investor is at a particular location may be by way of bar code tags 1070 carried or worn by an investor and read at various locations by bar code readers 1075. The Ibutton™ technology may also be employed as a form of an electronic time clock. Alternatively, the investor may be given an ID card that he/she passes through an electronic time clock upon arrival and upon exiting a facility. The ID card could be used for a period of time, e.g., one month, during which the card stores data verifying the visits to the facility and the duration of the visits. These cards could be returned to the behavior investment service provider where the data is read into the server 100 for updating an investor's relevant behavior activity and allocating credit accordingly.

Further still, one or more transponders 1080 may be deployed at locations or sites where activity is to be captured indicating presence of an investor. These transponders 1080 periodically, or when polled by another device, transmit a wireless radio frequency signal, infrared signal, audio signal, or other signal that is received by, for example a portable read/write (two-way) capable miniature memory chip device 1060 carried or worn by an investor or a portable RFID read/write capable device. An example of a portable Ibutton™ reader/writer device is the Model PIR1 manufactured and distributed by Embedded Data Systems. The data captured from a transponder 1080 by the investor carried or worn reader devices are then uploaded to the behavior investment server 100. Other examples of data collection devices are cards that store information on a magnetic stripe and are read or written to by a reader device.

As will be described hereinafter, the activity data capture devices 1000 shown in FIG. 2 are also representative of the types of devices that may be used to track and verify the specific nature, time, place and duration of wellness and healthy activities that may be relevant to a health-oriented behavior investment plan.

The data captured by one or more of the data captured devices is uploaded to the behavior investment server 100 by way of the network 900. In some cases, additional MODEM devices may be required or integrated into the data capture devices, as is known in the art and omitted in FIG. 2 for simplicity.

Figure 3:
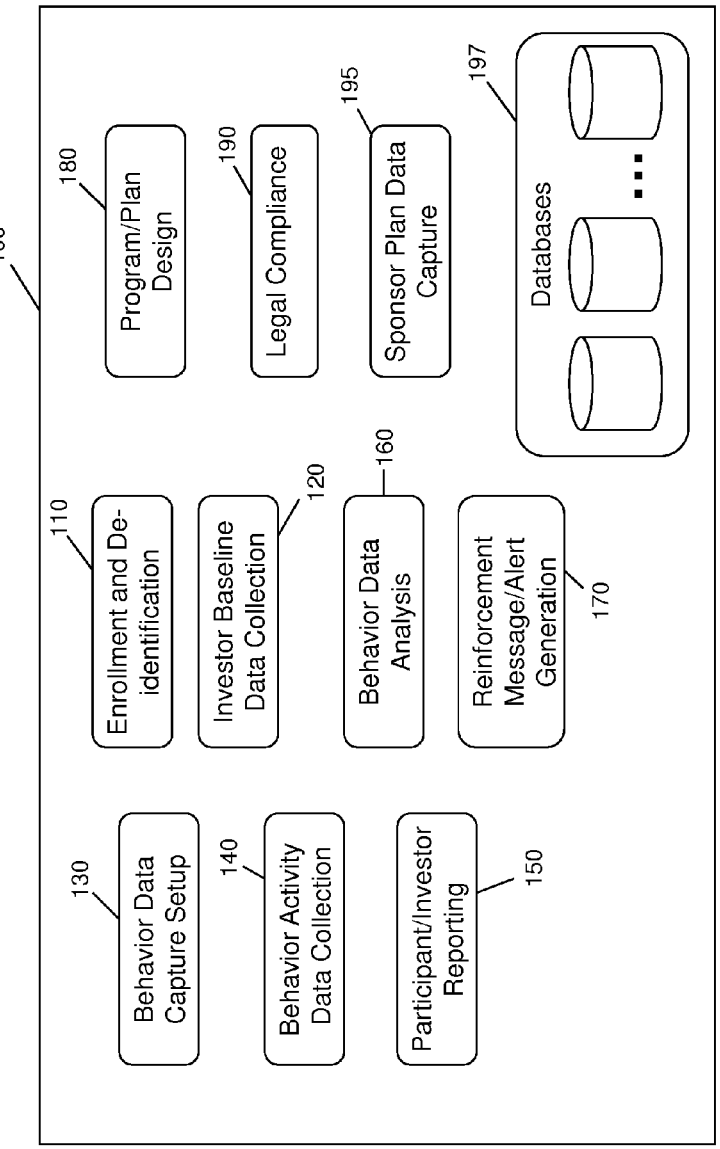
FIG. 3 is a block diagram showing the various modules of a behavior investment server according to an embodiment of the present invention.

Reference is now made to FIG. 3 where the various software modules executed by the behavior investment server 100 are shown. These modules are representative of the various functions of the behavior investment server 100, but it is not meant to limit the nature or degree of functions that may be performed by the behavior investment server 100. There are an enrollment and de-identification module 110, an investor baseline data collection module 120, a behavior activity data capture setup module 130, a behavior activity data collection module 140, a participant/investor reporting module 150, a behavior data analysis module 160, a reinforcement message/alert generation module 170, a program/plan design module 180, a legal compliance module 190, a sponsor plan data capture module 195 and a database system 197 comprising one or more data storage devices and associated database management software. Each of these modules is described in more detail hereinafter.

Figure 4:
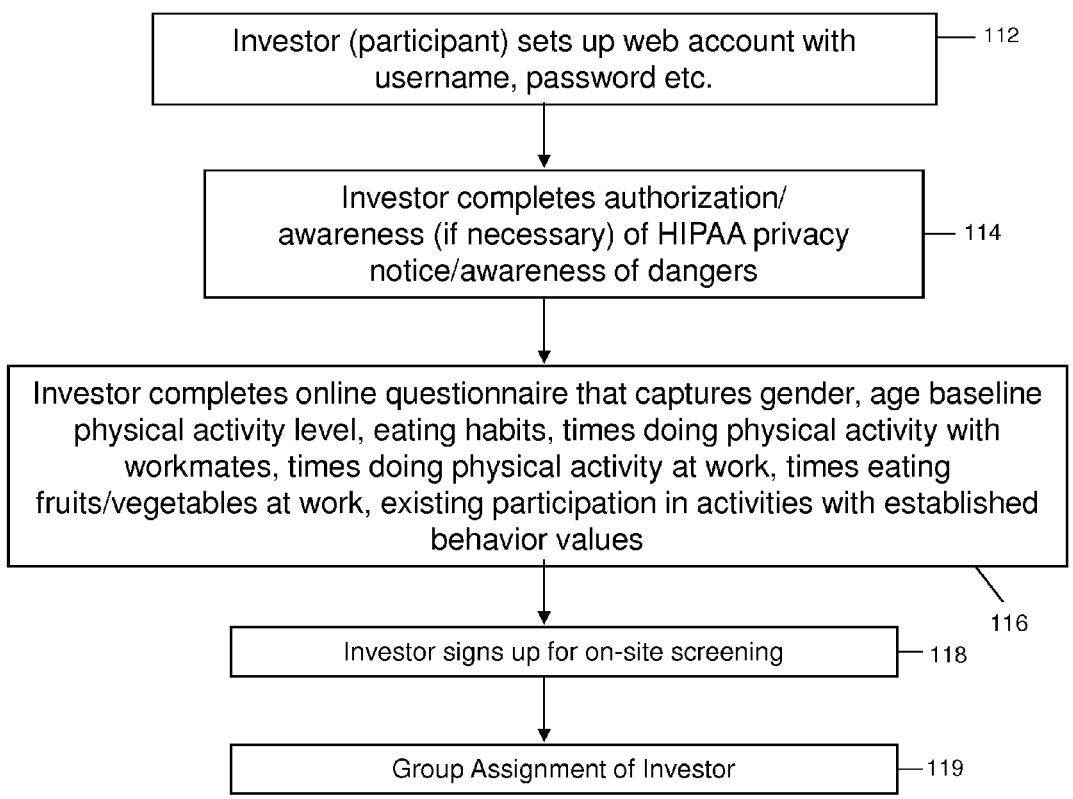
FIG. 4 is a flow chart depicting an enrollment process according to an embodiment.

FIG. 4 illustrates a flow chart for functions of the enrollment/de-identification module 110. The purpose of the enrollment/de-identification module 110 is to receive information from an individual to enable the individual to become a participant or investor associated with a behavior investment plan. During the enrollment process, an individual may communicate with the behavior investment server 100 through any means heretofore known or hereinafter developed, such as on-line computer access through the Internet, telephone, etc. At 112, an investor sets up an account with the behavior investment server 100 including a password and user name. At this time, the server 100 may confirm a person's eligibility to use the system and his or her gender. Also at this time, the investor is de-identified by assigning a code or account number for the investor that in no way reveals the identity of the investor. The de-identifying code or account assigned to the investor is associated with data that the behavior investment server 100 accumulates for that participant, and may under certain circumstances share with other entities. At 114, an investor is presented with the terms and conditions for using the system and is allowed to acknowledge/review the privacy and security notices explaining how personal information is protected by the server 100. The disclosures presented in 114 may include those that are associated with established laws or regulations, such as the Health Insurance Portability and Accountability Act HIPAA).

At 116, the investor completes a questionnaire that may capture information about the investor relevant to a particular type of behavior investment plan. For example, for a health benefits plan, the information captured from the investor include gender, age, baseline physical activity level, eating habits, frequency of physical activity with colleagues/co-workers, amount of physical activity associated with or at work, amount of consumption of fruits/vegetables at work, and in general existing participation in activities with established behavior values. An investor may also indicate his/her literacy level and/or language preference.

At 118, an investor may schedule an on-site screening that is tailored to the particular behavior investment plan.

Other functions performed during the enrollment process may include allowing an investor to purchase equipment necessary for participation in the behavior investment plan, such as one of the activity data capture devices shown in FIG. 2.

Still another function performed during the enrollment process is shown at 119 where an investor is assigned to one or more groups or teams depending on the parameters associated with the behavior investment plan. In one embodiment, the server 100 may automatically assign the investor to one of a plurality of groups or teams. For example, an employer may wish to divide its employees up into groups by department, location, function, etc., to allow the groups to compete against each other as part of the behavior investment plan. In another embodiment, the server 100 may automatically identify groups or teams for which the investor is eligible and permit the investor to select membership in one or more of the groups or teams for which the investor is eligible.

Figure 5:
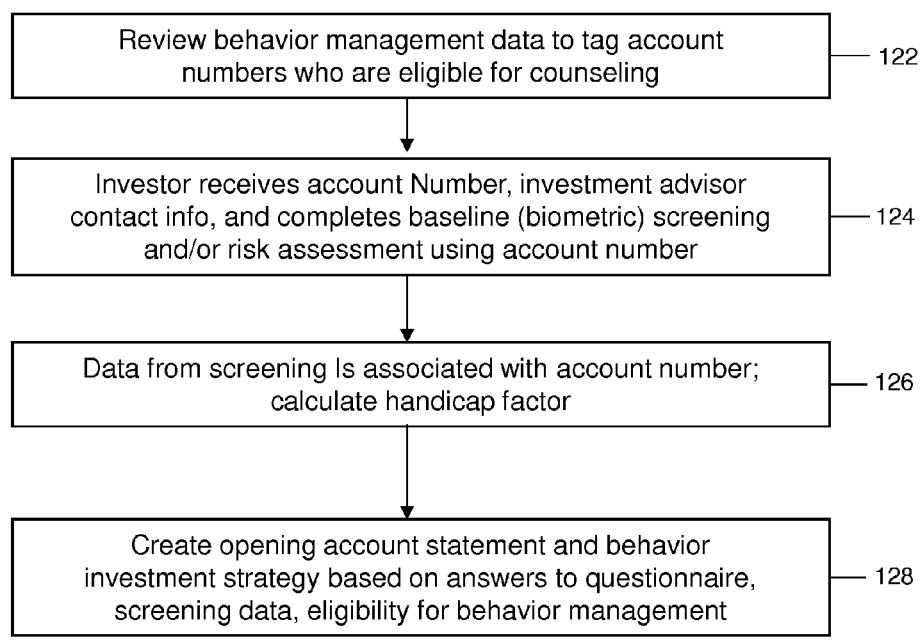
FIG. 5 is a flow chart depicting a baseline data collection process according to an embodiment.

The baseline data collection module 120 is now described with reference to FIG. 5. The baseline data collection module 120 captures and stores data or measurements related to the one or more desired behaviors or its/their impact on the one or more desired behaviors for each participant. For example, each participant may have certain mental, physical or biological conditions that affect that participant's ability to progress to the behavior goals. The baseline data or measurements allow the system to fairly measure the impact of a behavior related activity and to compare a participant's progress in the behavior reinforcement program with the progress of other participants. In addition to data collection, this module also performs some initial screening functions as will become apparent hereinafter. After all of the investors of a behavior investment plan have set up accounts with the server, then at 122, the server reviews the data entered by the investor and associated with his or her account number and identifies or tags those accounts that are eligible for special treatment, such as behavior management counseling. For example, an investor whose account number has been associated with screenings or assessments that indicate diabetes may be tagged as a person who is eligible for a specialized diabetes management service that is designed to optimize the health of the investor. At 124, the server 100 contacts each investor and provides the investor's de-identified account number, the contact information for any investment advisor/consultant associated with a behavior management service provider, and the investor completes some baseline behavior screening and/or risk assessment.

The type of data received about an investor during the baseline screening process depends on the nature of the behavior investment plan. For example, the server may provide a more detailed health status assessment questionnaire by which the investor provides specific information about current behaviors and health status, as well as information about energy levels and productivity. More detailed biometric data may be obtained for an investor through a live screening or a biometric screening kiosk apparatus. In fact, investors may earn awards for periodically visiting a biometric kiosk apparatus as is described hereinafter.

Also at 124, an investor may provide his or her account number to an authorized person other than the investor, who may then identify him or herself and then record the investor's biometric measurements such as (in the case of a health benefits plan) weight, body mass index, height, glucose levels for association with the account number a database. Similarly, an investor may provide his or her account number to an authorized person other than the investor, who may then identify him or herself and then verify and record the investor's proof of age for association with the account number in a database.

At 126, the data obtained from the screening at 124 is associated with the investor's account number. In addition, at 126, the server 100 computes a handicapping factor for an investor based on that investor's baseline data or measurements. The handicapping factor enables the system to fairly evaluate the impact (and thus credit) allocated to an investor for engaging in particular behavior related activity, and allows the system to fairly compare that investor's progress with other investors for purposes of establishing competitions or challenges for rewards or incentives between investors whenever the difficulty of a challenge may be significantly affected by physical or mental limitations. The handicapping factor may be computed based on biometric screening data (age, gender, etc.), availability of resources necessary to achieve the desired behavior, different physical or environmental barriers to the desired behavior, etc.

At 128, the server creates an opening account statement and behavior investment strategy based on the investor's answers to questions, screening data and eligibility of behavior management service.

After an investor has completed the enrollment process or the baseline data collection process, the server 100 may present the investor with the tools appropriate for the program, instructions for using the tools and rules of the program. The server 100 may credit the investor with investing BehaviorBux for reviewing the educational segment and passing a quiz comprising several questions related to the rules of the program.

Similar to investor registration with the server 100, program administrators establish accounts with the server and receive tools needed to prove on-site behavior education or promotion activities. Program administrators may also access instructions about tools when they log into the server and may access group data if the program administrator has the necessary privileges or authority (e.g., the administrator is an HIPAA-authorized individual or the number of participants is sufficiently large so as to render the data de-identified).

The behavior data capture setup module 130 is a module by which the types of (and manner of capturing) behavior activity data for a behavior investment plan are registered with the server 100 and made available to the behavior data analysis module 160. As one example, the sponsor or program administrator may label location marker devices in a manner that communicates location and relative location. That is, a location marker at the bottom of the stairs is always labeled by the name of the stairwell and the floor number, so that the behavior activity data collection module 140 may easily calculate the direction of the stair climbing, floors climbed, and location of the stairwell. The types of devices that may be suitable for use as location markers are shown in FIG. 2, and include RFID readers in conjunction with portable or wearable RFID tags, electronic time clocks, memory chip device readers in conjunction with miniature memory chip devices, bar code readers in conjunction with bar code tags, as well as transponders in conjunction with personal area network (PAN) devices, read/write capable RFID devices and read/write capable memory chip devices. In addition, a marker on a walking route might always be labeled by the mile mark from a starting location marker. The sponsor or program administrator may assign identifiers to data capture devices/identity devices so they may be used in combination with a location marker device to record the identity of the investor and the time and date the investor passes by or touches the location marker device.

In another embodiment, the sponsor or program administrator may assign an identifier to an activity data capture device so that its handshake with a particular location marker may be used to communicate a special meaning when interpreted with subsequent data handshakes at that location marker which immediately follow. The behavior investment server 100 may configure an activity data capture device that ensures that any data handshakes by an investor within a predetermined period of time (e.g., 10 minutes) of a certain type of data handshake receive special reinforcement. For example, a particular behavior management service provider such as a cardiac therapy provider has a reader device that ensures that the cardiac therapy provider's data handshake preceded or followed by an investor's data handshake through his or her complimentary device (RFID device, bar code tag, Ibutton™ device, etc.) at the same reader device within a predetermined period of time of each other (e.g., 2 minutes) is interpreted by the behavior investment server 100 as proof of that investor's participation in medical counseling and simultaneous authorization of reinforcement of the participation. Similarly, a health fitness instructor may have a reader device that interprets two reads/scans (or data handshakes) of a particular investor's complimentary device within a predetermined period of time as an indication that the investor participant in a fitness program. It should be understood that the same reader device can be used to indicate different activities. For example, detecting an instructor's wand at reader device A followed by investor's wand at reader device A is interpreted by the server 100 to mean that the investor attended instruction.

The behavior data capture set up module 130 is also used to establish parameters for recognizing certain purchases made by an investor at a POS terminal. Certain types of products/services may be associated with a desired behavior and used to assign investment credit to the investor. Conversely, the set up module 130 may be configured to allow investors to redeem accumulated investor credit or points associated with their achievement of behavior change goals to purchase merchandise or services by passing a suitable investor identifier device through a POS terminal at the supplier of the goods or services. Another variation of the POS terminal is a vending machine. The set up module 130 may be configured to allow an investor to self-identify himself/herself and purchase items with investor credit or points at a vending machine and/or capture proof of investor purchases of items associated with the desired behavior and make the data available to the behavior data analysis module 160.

The behavior data capture set up module 130 may configure parameters associated with an interactive voice response system to interact with investors. For example, the interactive voice response system may be configured to allow users to self-identify, prove their presence at a location relevant to a desired behavior (through use of the landline phone at the location, GPS device or other location technology), receive an auditory reinforcement of the activity, and capture the proof of presence data for analysis by the behavior data analysis module 160.

Examples of other configurations that are made by the behavior data set-up module 130 are:

The arrangement by which an investor proves the desired behavior by wearing an activity monitor that automatically transmits the proof electronically to the server 100. Examples of such devices are described above in connection with FIG. 2.

The arrangement by which data from two or more data capture devices are compared to further verify the authenticity of reported behavior.

The arrangement by which investors may record their presence and the date and time of their presence at different locations while receiving an auditory or visual reinforcement (using any kind of technology capable of achieving this goal—such as a time clock system, telephone system, RFID or GPS device).

The particular mechanism by which an activity data capture device transmits or sends data to the server 100.

A software function that interprets data collected through a location-marker activity data capture device and proves that the investor account number to which the data capture device is assigned should be credited as having performed the activity indicated by the location marker in combination with any other "indicator" data collection devices used before or after the relevant handshake with the location-marker.

A software function that analyzes the timing of the data handshakes to identify a group's (multiple investors') performance of a desired behavior (e.g., exercise at a fitness club). For example, if two investors (through their person activity data capture devices) conduct data handshakes at the same location marker within a predetermined period of time (e.g., one minute), each investor is awarded credit for doing the activity themselves and credit for engaging another investor to do the activity.

The behavior activity data capture devices need to be installed at the various locations before data can be collected from them for use in connection with the behavior investment plan. New activity data capture devices may be added to a behavior investment plan already in existence.

The module 130 may also be configured to deliver to a participant, depending on the manner of activity data capture, reinforcement communications to a participant at the time that activity data is collected. The reinforcement communications are designed to reinforce the participant's progress towards, and achievement, of the one or more desired behaviors. For example, the reinforcement communications may be a text message if the participant is uploading the activity data himself/herself via a PC or other device, a (pre-recorded) voice message if the collection of the activity data or occurrence of the activity is by way of telephone communications, other audio (alerts, celebratory music clips, etc.) if by way of a telephone, mobile phone, PC or other suitable participant portable device, or vibration on a mobile phone, etc.

The behavior activity data collection module 140 is the software function that collects the activity data captured by the various activity data capture devices for storage in association with an investor's account number in one of the databases 197 and for analysis by the behavior data analysis module 160.

The participant/investor reporting module 150 generates the various reports of investor performance based on the data analysis performed by the behavior data analysis module 160. Examples of the various reports are described hereinafter.

The behavior data analysis module 160 analyzes the data captured by the activity data collection devices for investors in order to compute and assign credit to behavior related activities of an investor. In doing so, the behavior data analysis module computes, for each investor, performance measurement data that represents a participant's progress with respect to achievement of one or more desired behaviors based on the captured activity data received for that participant/investor. In addition, the behavior data analysis module 160 compares the performance measurement data for a particular investor with respect to one or more other participants using the handicapping factors for the particular investor and for the one or more other investors.

The participant investor/reporting module 150 receives data from the behavior analysis module 160 to report to investors as described below. The behavior data analysis module performs many functions, examples of which are described below.

Assignment or investor selection of behavior goals. Investors may be assigned or may select goals regarding the desired behavior and receive reinforcement for achieving those goals. Examples of reinforcements are credit or point levels, incentives, recognition, employee benefit plan discounts, charitable contributions, etc.

Categorizing Investors. Investors may be categorized as beginner behavior-adopters, active adopters and counselors based on their accomplishment of different requirements with respect to adoption and maintenance of the desired behavior and demonstrated ability to mentor others in adopting the desired behavior. Beginner behavior-adopters may receive reinforcement through awards, messaging and wearable badges for achieving active adopter status. Active behavior-adopters may receive reinforcement through awards, messaging, and wearable badges for achieving counselor status. Counselors may receive reinforcement for continually mentoring beginner and active behavior-adopters. The behavior data analysis module 160 may award credits or points to counselors based on a percentage of the awards and reinforcements earned by those beginner and active behavior-adopters on their "team". Thus, a "pyramid" rewarding scheme may be implemented whereby counselors receive a share in the award credits of each of their subordinate investors that they mentor. The behavior data analysis module tracks each counselor's share of awards earned by those in their team.

A group of investors or a program sponsor (such as a corporation or religious congregation) may be categorized as a beginner behavior-adopter, active adopter or counselor based on group members' verified accomplishment of different requirements with respect to adoption and maintenance of the desired behavior and demonstrated ability to mentor other groups in adopting the desired behavior. Beginner-level organization behavior-adopters may receive reinforcement through awards, messaging and branding for achieving active behavior-adopter status. Active-level organization behavior-adopters may receive reinforcement through awards, messaging, branding and public recognition for achieving counselor-level organization status. Counselor-level organizations receive reinforcement, such as tax breaks, public service announcements, subsidies, insurance premium discounts, branding and public recognition, etc., for continually mentoring beginner-level and active level behavior-adopter organizations that achieve and maintain the desired behaviors.

Furthermore, the behavior data analysis module 160 may categorize investors in different ways based on data collected about them so as to identify the reinforcement messaging most likely to bring about the desired behavior.

Group Reporting. The behavior data analysis module 160 generates reports about the behaviors of investors by individual, group and teams reports. Reports may be automatically generated and delivered to individual investors, and group or team reports may be automatically generated and delivered to media contacts in the immediate group of investors, at charity partners and in the larger community of groups or teams.

Adjustment for Handicap Factor. When computing performance of an investor (or a group of investors) for comparison in a competition or challenge with other investors (or groups of investors), the data analysis module 160 adjusts the performance achievement based on the handicap factor for each investor.

Investment Opportunities and Policy. The data analysis module 160 may analyze an inventor's baseline screening data and generate a list of behavioral "investment opportunities" that are particularly relevant to the investor, such as visits to a fitness facility, walking loops around the walking path near the investor's office, etc. Moreover, the data analysis module 160 may analyze the baseline screening data to create an "investment policy" for the investor that outlines recommended behavior "investments" and describes opportunities for such "investments" that are relevant for the investor. Similarly, the baseline screening data for a group of investors may be analyzed together with an assessment of the environmental conditions of the group to create an "investment policy" for the group that outlines recommended environmental changes, communications to group members and outside parties, such as health and benefit plan designs that are relevant for the investors in a group.

The data analysis module 160 may also analyze baseline screening information and questionnaire response information to compute or express an impact of the investor's current detrimental behavior or poor health status on his or her personal financial state, the good of society, the earth, or other affected groups or persons, or similarly to express the impact of an investor group's current detrimental behavior or poor health status on the sponsoring organization's financial state, the good of society, the earth, or other affected groups or persons.

The reinforcement message/alert generation module 170 is responsive to commands from other modules, such as the behavior data analysis module 160 and reporting module 150 to deliver reinforcement messages to an investor or group of investors. An investor may select the specific manner by which the messages are delivered to him/her. Examples of reinforcement messages are explained below.

Encouragement messages (video or audio) by program administrators, sponsor officers, celebrities, comedians, investors, investor's family members or champions of the desired behavior may be recorded for delivery to investors. These messages may be recorded early on in, or during, the behavior investment plan and stored in one of the databases 197 for later retrieval and delivery at the appropriate time for presentation to an investor. The messages may be delivered by way of a video clip or audio clip to an investor during an investor log-in session with the server 100, email messages to an investor, audio, video or photo messages to an investor's mobile phone devices, etc. The data analysis module 160 determines when it is appropriate to deliver a message to an investor based on the investor's performance accomplishments, lack of accomplishments, recent period of inactivity, recent period of activity, activity or performance of other investors involved in a challenge or competition, etc. Investors may reinforce themselves or other investors by creating personalized messaging (electronic, telephonic, video, etc.) that is stored in one of the databases 197 for delivery upon investor achievement or lack of achievement of goals related to the desired behavior.

Advertisers and/or sponsor entities who wish to earn goodwill with investors may generate and record congratulatory messages that are sent to investors upon investors achieving goals and/or maintaining the desired behavior. Moreover, the congratulatory messages may be accompanied by award incentives, charitable contributions and other reinforcements (with or without a congratulatory message), but without the advertiser ever gaining knowledge of the identity of an investor. Further still, advertisers and sponsors may obtain (de-identified) information from the server 100 about a target population in order to create content and surveys to obtain additional useful information from investors and offer useful information to them, again without gaining access to the identities of the investors.

Other types of reinforcement messages may include information about incentives that an investor is entitled to or has earned. The data analysis module 160 analyzes the baseline screening data and computes the incentives or rewards for which the investor may be eligible based on parameters of the plan design. Information about these incentives is communicated in messages to the investor by the message generation module 170. Similarly, messages may be generated to present (e.g., display) rules and communication materials about challenges or programs for which the user is eligible, terms of an agreement to earn rewards or incentives on another person's behalf or to donate rewards or incentives to charity, An investor may also authorize scheduled reporting of or access to his/her information to any individual employed by an entity that is directly subject to HIPAA privacy and security laws (such as a physician, pharmacist, psychologist, nutritionist, health insurer, employees of a health plan sponsor that operate the health plan, or physical therapist) or to an entity that is a "business associate" to an entity subject to HIPAA privacy and security laws (disease management counselor, actuarial or consulting firm for a health plan, third party administrator of a health plan, insurance broker, wellness program provider, employee assistance provider, or wellness coach) for any purpose, such as professional reinforcement of the desired behavior.

The program design module 180 is used to allow a sponsor and/or consultant to define the parameters associated with a behavior investment plan. It is here that the server 100 is configured to analyze the baseline screening information, workplace assessment questionnaires, etc., to calculate the economic impact of differing percentages of investors achieving the desired behavior. This module may identify recommended changes to the workplace environment to remove perceived barriers to the desired behavior that exist in the workplace environment.

Moreover, the program sponsor may provide information about the location and distance of environmental resources that may be used for physical activity (such as walking routes, stairs, on-site fitness centers) and information about other resources that promote the desired behavior to recommend placement and which can be used in the naming of location marker devices for purposes of activity data capturing. Likewise, the program sponsor may provide information about the kinds of resources that may be used to promote healthy eating to recommend placement and usage of POS and vending system activity data capturing tools.

The plan design module 180 may also generate a recommended behavior change program with credit or point values for standard activities and values for environment specific activities based on the average amount of effort expended to achieve the behavior and/or the perceived desirability of the behavior, as well as incentives and recommendations for achieving such goals. For example, climbing 20 floors of stairs is equal to 20 BehaviorBux, completing an effectiveness survey is equal to 100 BehaviorBux.

The legal compliance module 190 manages security procedures that may be necessary to comply with industry standard and/or legal regulations. One example of such compliance requirements are the HIPAA privacy and security procedures for health related information. The legal compliance module 190 manage what is referred to as an "organized health care arrangement" comprised of the health plan or health care provider, any employees of the health plan sponsor identified as eligible to use "protected health information" for purposes permitted by law, and all business associates to the health plan and/or health care providers that must access "protected health information" in order to operate the behavior change program or analyze its effectiveness. This module also manages a set of HIPAA authorizations by which investors may permit non-HIPAA entities access to their biometric or behavior information and a set of HIPAA revocations by which users may revoke prior authorizations.

The legal compliance module 190 creates a set of privacy and security procedures and contracts for the behavior investment program that establish confidentiality and security obligations and data use and sharing obligations and restrictions among every entity that uses biometric and behavior information in order to operate the behavior investment program when it is not incorporated into a HIPAA covered health plan or provided by a HIPAA covered health care provider. Each investor will be provided with an online, telephone or other electronic mechanism that requires the investor to acknowledge review of a HIPAA or other kind of privacy notice that describes how biometric and behavior information is used.

Furthermore, the module 190 implements an online, telephonic or other electronic mechanism that automatically grants access to "de-identified" information to any individual who uses a password provided to an entity that is directly subject to HIPAA privacy and security laws (such as a physician, pharmacist, psychologist, nutritionist, health insurer, employees of a health plan sponsor that operate the health plan, or physical therapist), or any individual who uses the password provided to an entity that is a "business associate" to an entity subject to HIPAA privacy and security laws (such as a disease management counselor, actuarial or consulting firm for a health plan, third party administrator of a health plan, insurance broker, wellness program provider, employee assistance provider, or wellness coach). These individuals may re-identify the information as needed because they have been provided with the re-identification key pursuant to their proof of HIPAA compliance.

Further still, the legal compliance module 190 may implement an online, telephonic or other electronic mechanism that enables an investor to create for distribution to others a report from the investor's confidential information that does not include the investor's account number.

The sponsor plan data capture module 195 captures information from the program sponsor and investors about the work environment and its effect on the desired behavior (such as food offerings and its effect on weight maintenance). This module also manages data provided by a program sponsor relevant to the potential economic impact of increasing the desired behavior among its population (such as absenteeism, health claims data, age distribution, disability claims data and workers compensation data). Investors and/or the program sponsor may provide information to this module about eligible individuals who model the desired behavior and should serve as leaders for the behavior investment program, about existing environmental or third-party resources that promote the desired behavior, and existing smaller communities that may serve as teams in competitions aimed at promoting the desired activity and contact information for the leaders of those communities.

Figure 6:
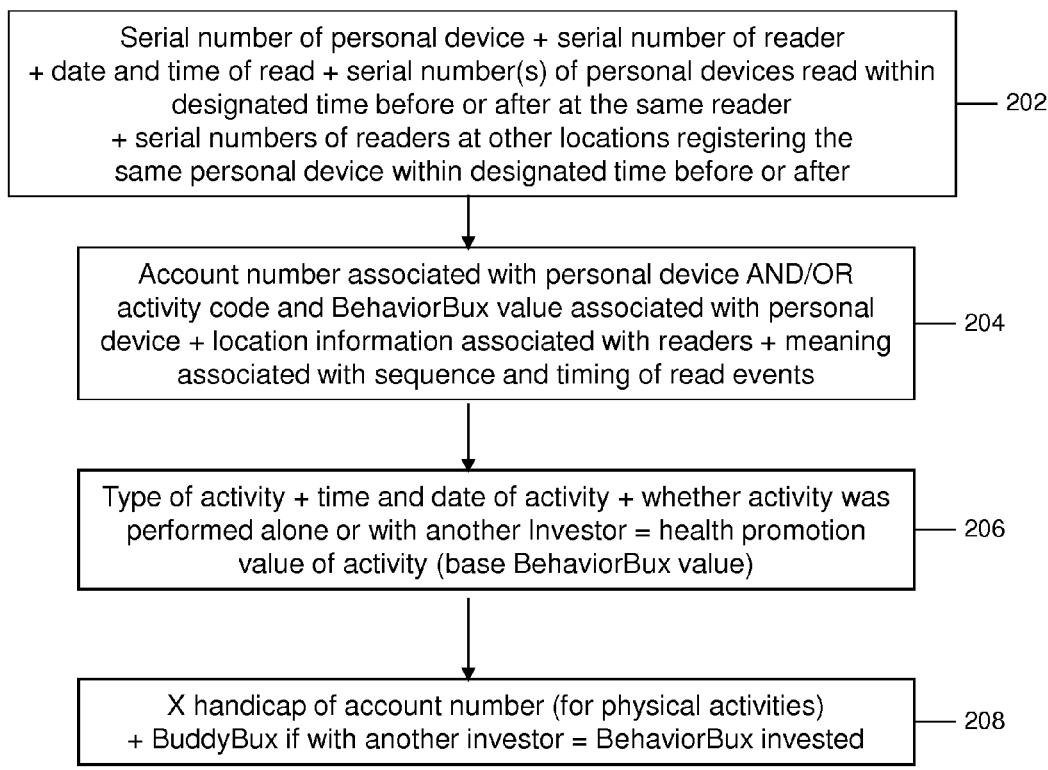
FIG. 6 is a flow chart depicting an example of an activity data capturing and report computations made from devices that have recorded an investor's physical activity according to one embodiment of the invention.

Reference is now made to FIG. 6 in which a description is provided of a computation made by the data analysis module 160 based on activity data collected from electronic activity data capture devices, examples of which are shown in FIG. 2. For purpose of this example, the relevant activity data capture devices may comprise an RFID reader at a particular physical location that reads an RFID tag worn or carried by an investor, a memory chip reader at a particular physical location in that reads a miniature memory chip device carried or worn by an investor, a bar code reader that reads a bar code tag carried or worn by an investor or an electronic time lock at a particular location that reads an ID card carried or worn by an investor. Alternatively, the relevant activity data capture devices may comprise transponders positioned at various locations or sites and investor-worn or carried personal area network devices, read/write capable RFID devices or read/write capable memory chip devices. The device that is carried or worn by the investor is referred to herein as the "personal device" and the device that reads data from the personal device is referred as the reader.

At 202, the behavior data analysis module 160 analyzes from the relevant data activity collection devices the serial number (or other identifier) of the personal device that has been read, the serial number (or other identifier) of the reader device and the date and time of the read event. Alternatively, the investor or an agent of the investor may enter a code at the time that the personal device is read to further assist the server in identifying the investor.

In addition, the data analysis module 160 analyzes whether the serial number of personal devices are read within a predetermined time interval at the same reader to interpret that the investor associated with same personal device is attempting to register or prove a particular activity, or whether a first investor associated with one personal device should be given credit for the behavior activity of a second investor who closely follows the first investor at the reader device.

At 204, the data analysis module 160 retrieves the account number associated with the personal device or a code entered at that time, the credit to be awarded to that investor (herein referred to as BehaviorBux value), the location information associated with the readers and any relevant meaning associated with the sequence and timing of read events (examples of which are described above). Thus, the meaning associated with two read events of the same personal device by the same reader within a predetermined time interval is retrieved. Another meaning that may be given to a particular sequence of read events is to determine whether the serial numbers of reader devices at other locations read the same personal device within a predetermined time interval. This may indicate that an investor has engaged in a particular sequence of positive behavior activities for which special credit should be given to the investor.

Next, at 206, the data analysis module 160 analyzes the type of activity associated with the read events, the time and date of the activity, whether the activity was performed alone or with another investor to determine a base credit or BehaviorBux value for the investor.

At 208, the data analysis module 160 adjusts the base BehaviorBux value based on the handicap factor (described above) and also adds credit for engaging in the activity with another investor, called BuddyBux.

The activity collection process shown in FIG. 6 may be used to encourage the use of stairwells rather than elevators. For example, RFID, barcode, magnetic-stripe, keypad or similar readers/detection devices are installed, preferably, on each floor of a building stairwell (in an employer's building, for example) and the investor would be credited for taking the stairs. Such readers/detection devices may be configured to automatically detect when the participating member passed nearby. Preferably, the investor may be required to voluntarily swipe his ID card or other personal device near or through a reader or a transponder. The moment of data capture is signaled by a distinct sound that immediately reinforces the activity. A weighted score is calculated based on a number of factors including, for example, how fast the stairs are taken, the impact handicap factor of the investor, the number of flights of stairs that are taken, and whether the investor went up or down the stairs.

Figure 7:
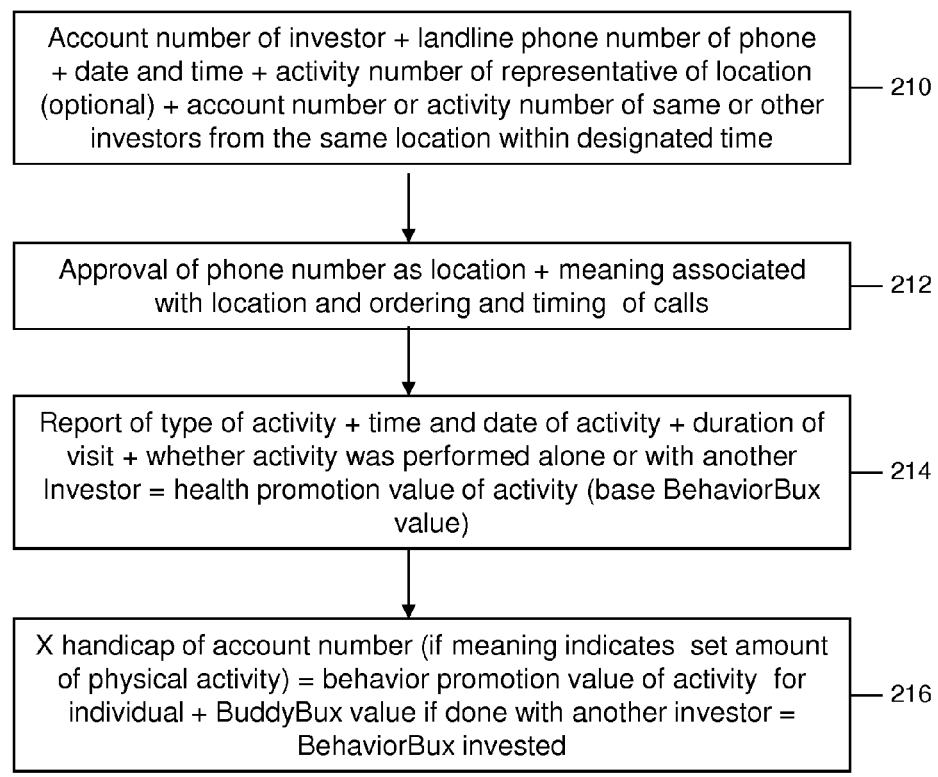
FIG. 7 is a flow chart depicting an example of a telephone-based activity data capturing and report computation according to an embodiment of the invention.

Turning to FIG. 7, another example of an activity data capturing process is described. In this example, the investor calls into the server 100 from a telephone (landline or wireless) at a location associated with a behavior related activity. For example, the location may be a fitness facility, health services seminar site, etc. At 210, the investor calls into the server 100 using a phone number that the server 100 recognizes as being associated with a corresponding behavior related activity. The investor making the call enters his/her account number and the server 100 captures the telephone number from which the call is made and the date and time of the call. Additional information may be entered such as an activity number of a particular representative or service provider associated with that location. In addition, if the investor is attending the behavior related activity with another investor, the account number and related information of the other investor(s) is noted by the server if entered within a predetermined period of time that is interpreted by the server as being worthy of BuddyBux credit.

At 212, the server 100 compares the telephone number of the incoming call with data stored in one of its databases to determine that is associated with an approved behavior related activity. In addition, the server 100 uses related stored information to determine the meaning associated with the call based on the data collected during the call (account number of one or several investors), the date and time of the call, etc. This meaning determines the amount of credit (BehaviorBux) to be awarded to an investor for the particular activity.

At 214, the server creates a report for storage in one of its databases based on the type of behavior related activity, the time and date of the activity, the duration of the activity and whether the activity was for one investor or for one investor who also is promoting the desired behavior of another investor. These pieces of information are used by the server 100 to compute the base BehaviorBux credit to be associated with the activity for the relevant investor(s).

At 216, the server 100 takes the base BehaviorBux credit value and applies an adjustment to it according to a handicap factor for that investor if the activity is one that requires such a handicap adjustment. The server 100 also adds any credit applicable to an investor for doing the activity with another investor, the so-called BuddyBux value, and adds this to the base BehaviorBux value to reach the total BehaviorBux invested for that activity for the investor.

Examples of uses of the process shown in FIG. 7 include an investor attending a support group or counseling session for alcohol or drug abuse rehabilitation. The reporting and verifying means may be a telephone call from the doctor or supervisor of the counseling session or group. The investor would give the person responsible for making the call his or her account number, a server-assigned code for the approved counseling activity, and the telephone number of the server's telephone data entry function. The behavior investment service provider may either staff a call center with individuals to receive calls of this type for other behavior management service providers, or may use an interactive voice response automated telephone system. The doctor or supervisor making the report provides a unique identification known only to that provider and to the behavior investment server as well as the account number of the investor that allows the system to know which participating member to credit. Thus, it is not possible for another person to call and falsely misrepresent untrue attendance. If the behavior investment service provider's call center or automated voice response system does not recognize the calling number as an approved known location, then the telephone operator or the interactive system asks the caller to record the name, address, phone number and contact name for the location. This information is recorded so that a representative of the behavior investment service provider can call and determine whether this location and activity meet the qualifications for allocating credit to an investor. If so desired the representative of the behavior management service provider may request the behavior investment service provider update its database to include this activity and location for future use.

Some fitness clubs or other preventative health services may not wish to allow their clients to take the time to make these telephone calls. In that case, other means may utilized in order to report and verify the attendance by a participating member, such as the electronic time clock, RFID equipment, Ibutton™ equipment, bar code reader equipment, transponders, etc., examples of which are described above in connection with FIG. 2.

Figure 8:
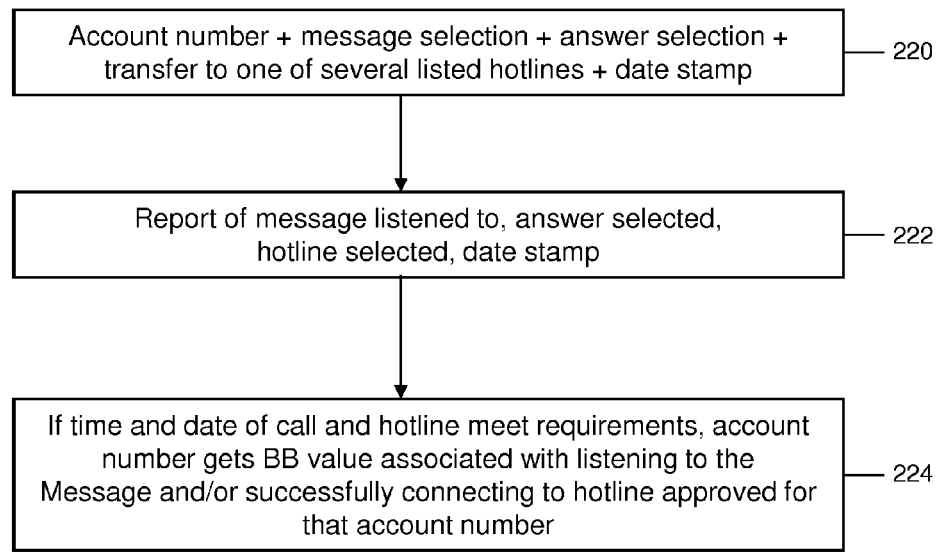
FIG. 8 is a flow chart depicting an automated voice interactive session by which an investor may earn credit according to an embodiment of the invention.

Reference is now made to FIG. 8 which illustrates still another activity data capture technique according to one embodiment. In this example, the activity is an automated phone counseling session. At 220, the investor calls into to an automated phone counseling service, enters his/her account number, makes certain message menu selections, answers one or more questions on a particular counseling topic, and may be transferred to a topic-related hotline number. The date and time of the session is also captured. At 222, the server generates a report on the data collected at 220 for storage in one of the databases. At 224, the server examines the data in the report produced at 222 from the session at 220, and if the time and date of the call, together with other requirements concerning the messages listened to and responses collected from the investor meet certain requirements (along with any hotline transfers the investor elected), the server allocates a certain BehaviorBux value to the investor's account for the activity.

Figure 9:
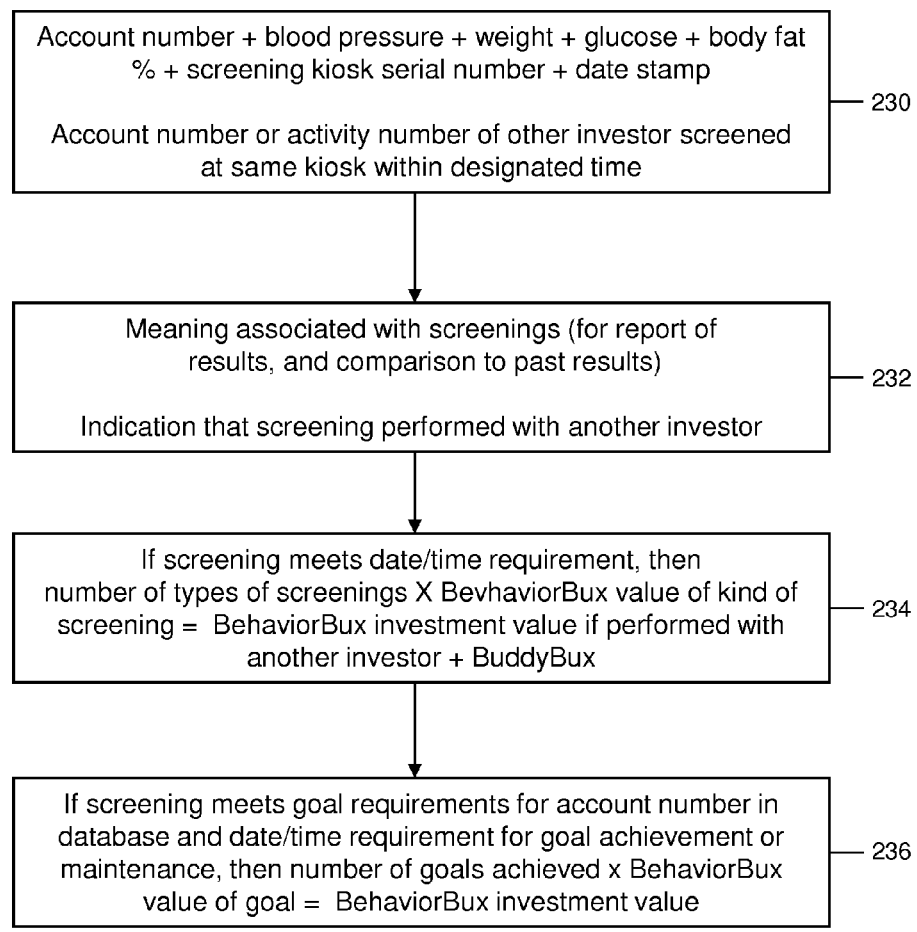
FIG. 9 is a flow chart depicting a biometric screen data capturing process and report computation according to an embodiment of the invention.

FIG. 9 illustrates an example activity data capture process for biometric screening of an investor. Biometric screening is an example of a health type behavior activity that is relevant to a health investment plan. A biometric screening may be performed at a kiosk device that is known and available to individuals to perform basic biometric screening data collections for upload to the server 100. Alternatively, the biometric screening may be performed by a physician during a visit to the physician's office, and uploaded electronically or manually (through user input) to the server 100.

At 230, the investor's account number is captured, together with various biometric parameters such as blood pressure, weight, glucose level, body fat percentage. This information is associated with the collecting entity, e.g., an identifier of the particular kiosk or of the physician, and the date of the data collection. At 232, the meaning associated with the biometric screening activity is determined, such as whether it is for purposes of establishing a baseline set of parameters, for purposes of comparison to prior results, etc.

At 234, the server 100 computes the baseline credit to be allocated to the biometric screening event. For example, the server 100 may have established a data and time requirement, the number and/or type of screening, etc. for a particular base BehaviorBux value. If an investor had the screening together with another investor, then the investor may receive BuddyBux credit for doing so.

At 236, the screening data itself is examined and compared with prior screening data or other goal related information for the investor to determine whether the investor should be allocated some goal or maintenance related credit. For example, if various goals are achieved in a particular biometric screening, the total credit allocated to the investor may be a product of the number of goals achieved and some BehaviorBux value of the goal, to produce the total investment value for the screening activity.

For those investors who participate in a health investment plan, and are considered high health risks, the system may be configured in a particular manner. Such high risk investors may provide their doctors with written consent to supply the behavior investment service provider with their specific examination or laboratory results. This would allow, in these special cases, for an individual who works for an insurance company to evaluate the investor's medical results and determine whether progress has been made and whether the server should allocate credit to the investor.

Figure 10:
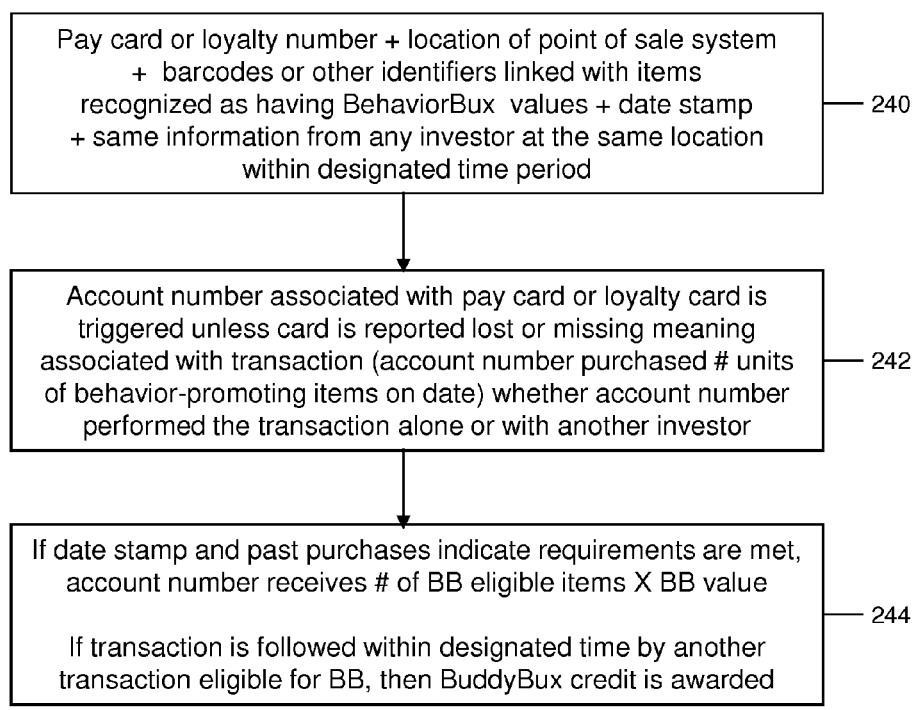
FIG. 10 is a flow chart depicting an example of a point-of-sale transaction data capturing and report computation according to an embodiment of the invention.

Referring now to FIG. 10, another activity data capture example is described for a point of sale transaction. In this type of activity data capture, a POS terminal is used to capture data associated with a purchase transaction related to a desired behavior. At 240, the investor purchases a product or service with a payment card (credit card, debit card, health account card, etc.) or uses a loyalty number when making a purchase. This information, together with the location or identifier of the POS terminal, product or service codes associated with items or services purchased (for which BehaviorBux credit is given) is captured from the POS terminal. In addition, the date of the transaction is captured, together with any similar information from any investor at the same location within a predetermined period of time.

At 242, the server 100 retrieves the account number for the investor based on the payment card or loyalty number in the captured transaction data. In addition, the server captures and stores, in association with that investor account number, the number of units of behavior-promoting items purchased and the date of the transaction, as well as whether the investor engaged in that transaction alone or with another investor in order to qualify for BuddyBux credit.

At 244, the server 100 analyzes the captured POS transaction data to determine whether it satisfies certain requirements based on date of the transaction and past purchases, and allocates the appropriate BehaviorBux credit value depending on the number of qualifying items in the transaction. In addition, the server allocates BuddyBux credit if the investor engaged in the transaction with another investor within the predetermined period of time.

One example of the process shown in FIG. 10 is for a cashier, for example, at a company cafeteria to initiate a data upload to the server 100 to allocate credit or points for the an investor. For example, the participating member's RFID tag, ID card, credit card, loyalty card, or other membership identification device is used to provide the investor's unique account number to the cash register or to a separate reporting device. The cashier may manually enter a code for each food item purchased by that member or the register automatically identifies the food items being purchased and sends such information along with the investor's account number to the server 100 for recordation and credit. It is thus possible to assign a credit to the purchase of a salad or vegetables, for example. Although not preferred, such feature could also be used to apply a negative credit for a poor food choice made by the investor in the company cafeteria. It is not necessary for this reporting device to send the information back to the server immediately; the data could be stored, updated, and sent one or two times each day to the databases.

Figure 11:
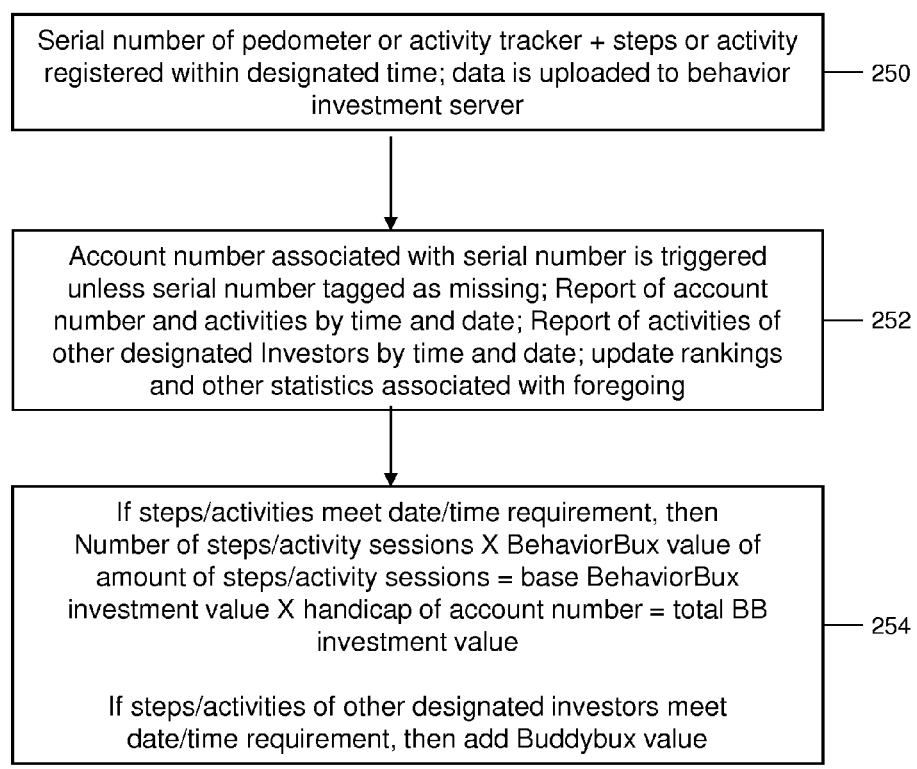
FIG. 11 is a flow chart depicting an example of a physical-activity monitor data capturing and report computation according to an embodiment of the invention.

Turning to FIG. 11, an activity tracking device, e.g., electronic pedometer, is described as another example of an activity data capture. In this example, the investor is wearing or is carrying a device that is capable of measuring, in real-time, the amount of activity that the investor is engaged in. This is particularly useful in a health-type behavior investment system in which the amount of a type of activity of an investor is used to allocate investment credit to an investor. At 250, the investor uploads data collected by the device to the server 100 by way of a personal computer, telephone, or a reader device that is connected to a PC or a network interface device (which is in turn connected to the Internet). At the time of the upload, an identifier of the device and the activity recorded by the device are uploaded to the server 100. The recorded activity may comprise the number of steps, distance traveled, etc., within a period of time. At 252, the server 100 associates the identifier of the device with the account number of the investor and generates a report for storage as to the captured activating by time and date. In addition, at 252, the server 100 generates a report of activities of other investors that may have uploaded similar data within a designated period of time. The server 100 may also update rankings and other statistics for the investor and for a group of which the investor is a member. At 254, the server 100 analyzes the data contained in the activity report to determine whether it meets certain minimum requirements (amount or degree of activity within a certain time interval) and the date and time of the activity. The server computes a credit amount to be allocated for the activity by the product of some activity measurement value (e.g., number of steps/activity sessions) and the BehaviorBux value for the steps in order to arrive at a baseline BehaviorBux investment value. The server may also adjust the baseline investment value for a handicap factor associated with the investor, if one is available, for purposes of comparison against other investors, etc. Further still, if another investor uploads his/her activity data close in time to such data uploaded by other designated investors (as part of a buddy group), then that investor may receive additional BuddyBux credits for promoting the desired behavior of other investors.

Figure 12:
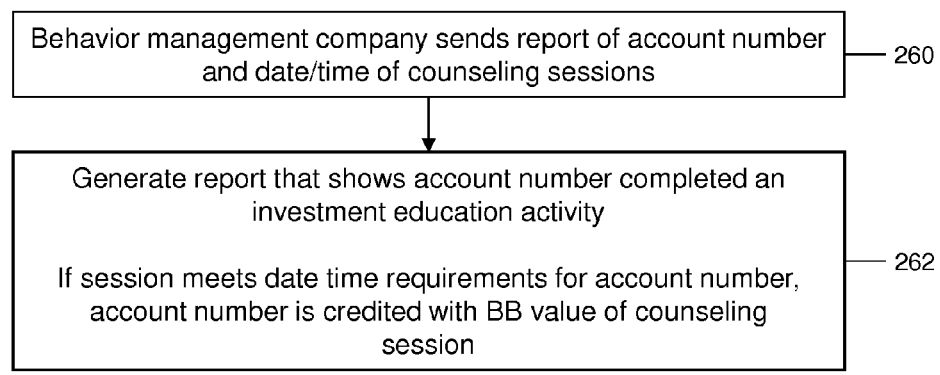
FIG. 12 is a flow chart depicting a data capturing and report computation for data from a behavior management service according to an embodiment of the invention.

FIG. 12 illustrates how data from a third party partner, such as a behavior management service provider, may be assimilated by the server 100 to allocate the appropriate investment value for an investor. At 260, the behavior management service provider sends, by way of email, web form, Internet file transfer, etc., a report containing the account number(s), date and time and nature associated with one or more counseling sessions conducted with an investor. The server, at 262, generates a report for storage in its databases, in association with the account number, the fact that the investor completed an investment education/counseling activity. If the counseling session report satisfies date and time requirements for that investor, then the server credits BehaviorBux value to the investor for that counseling session.

One example of the counseling activity session represented in FIG. 12 in which the investor receives so-called "cognitive therapy" by calling a hotline associated with a particular counseling function. The investor enters his/her account number after dialing the hotline number, and selects an option to plan the day's behavior promoting activities. The investor may be prompted to enter or record the food selections or health activities that the investor plans to engage in for the day. This is primarily designed to provide personal accountability back to the investor. Use of this function in and of itself is worth investment credit to the investor. A similar arrangement may be achieved through email or web based communication between the server 100 and an investor.

Figure 13:
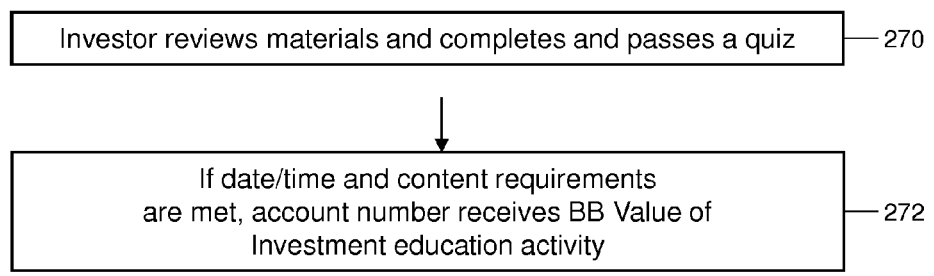
FIG. 13 is a flow chart depicting an education session and related data capturing and report computation according to an embodiment of the invention.

FIG. 13 illustrates how data from an education session may be assimilated by the server 100. At 270, an investor participates in an on-line, live in-person, or other education session and takes a quiz. If the investor achieves a minimum score on the quiz, then this information is (uploaded if sourced from a third party entity) stored by the server 100. At 272, the server 100 analyzes the date, time and contents of the education session, and allocates BehaviorBux investment credit to the account number of the participating investor(s).

FIG. 14 illustrates the types of reinforcement that may be communicated to investors according to an embodiment of the invention. The server 100 takes in the data concerning captured activities for investors and determines appropriate reinforcements to be delivered to investors. At 280, the server 100 generates two types of reinforcement in response or in association with received activity data. The first is an immediate reinforcement at the time that the activity data is uploaded to the server 100. Examples of immediate reinforcement are sound, text, light, and/or vibration to the investor to confirm that the activity data is collected. These types of reinforcements are particularly effective when the investor is uploading the activity data himself/herself. A text message may be delivered or displayed to a user when uploading the data from a PC or mobile phone, or other data device that has a display or speaker. The text message may include words of praise and/or encouragement to the user concerning the particularly activity data just uploaded.

The second type of reinforcement at 280 is one that is on a short-term periodic basis, such as weekly. For this type of reinforcement, the server 100 may analyze the types of activity data uploaded for an investor over a recent period of time, e.g., one week. In particular, the server 100 may generate a report for an investor as to the activities captured during that time interval, the types of activities and the dates. On a group level, the server 10 may report to all investors in a group (or a lead investor), the activities, types and dates uploaded for the group. The server 100 may also generate reports for that time interval as to the BehaviorBux earned/invested, the amount of additional investment required to achieve a particular milestone or dividend, and the degree to which the investor has advanced in a gaming situation by virtue of the activities captured for that time interval.

Examples of gaming situations are described below. The server 100 may allocate one of its databases to store electronic games that incorporate incentive points or credits earned by investors through exhibiting and maintaining the desired behavior. Alternatively, an investor may authorize release of his or her points or credits to outside electronic (or on-line) game providers for use in a game. The server 100 may allocate storage in one of its databases for entertainment modules that incorporate current incentive points or credits earned by the user through exhibiting and maintaining the desired behavior. Alternatively, an investor may authorize release of his or her current points or credits or summarized behavior information to an outside (on-line) entertainment entity for purposes of interactive entertainment.

At 282, the server generates longer term reinforcement messages. For example, the server may generate a message announcing a particular type of dividend awarded to an investor as a result of achieving a particular goal. The dividend may include points allocated to a point bank account that the investor can used to purchase merchandise or services, a deposit to a health savings account or flex account, reduction of an investor's insurance premium, phone encouragement messages, feedback/reinforcement messages from a counselor or doctor, etc.

FIG. 15 illustrates how the behavior investment server 100 uses its stored data to set up an integrated reward platform that is an Internet or intranet web site 290 accessible to investors. The site 290 may be a clearinghouse for performance and results of investors, communications related to an investment program, data from other databases (such as a wellness database) and investor/employee recognition information. Using this information, the site 290 may issue award points, manage on-line redemption and fulfillment of points, and may generate consolidated reports. This could be handled through the server 100 or through data sharing between the server 100 and an incentive fulfillment company, where the server 100 transmits data to an incentive fulfillment server data showing points earned through accomplishment of goals without revealing to the incentive fulfillment company how the points were earned.

Several additional features and capabilities of the system and method according to the present invention are now described. In the context of a health investment plan, the system may be used to automatically score a health risk assessment. The server 100 may automatically score an investor's health risk assessment based on biometric data received for the investor and questionnaire responses and provide the results and an explanation at the end of an investor's phone call into the server. The scoring and explanation may include suggestions for the investor to take certain actions, such as visit a dentist, get a cholesterol check, etc. The server 100 may include the capability of recording a reminder memo for the following a predetermined period of time later to follow up with the investor as to whether the investor has taken any of those suggested actions. The server stores the recorded reminder and places it in a virtual mailbox associated with the investor's account number. Later, the server 100 invokes an automated telephone system function that calls the investor and alerts him/her that there is a "reminder message in your BehaviorBux mailbox, please enter your account number to retrieve your secure message." The investor can call back later and enter his/her account number or enter the account number at that time to listen to the reminder. After the reminder plays to the investor, the server may ask if the investor has completed the recommended action. If so, the server may play a congratulation message. If not, the server may ask if the investor wants to record another reminder, or if the investor would like to request further support. A similar arrangement may be achieved through email or web based communication between the server 100 and an investor.

The system and method according to the embodiments of the present invention have unlimited applications and utility. Health is only one example of an embodiment. Moreover, the data collected by the system for investors (particularly in the context of a health investment plan), may be used for data mining purposes on a de-identified basis. For example, the behavior investment service provider may sell or license to service/product suppliers, insurance companies, actuaries, etc., access to its data collected over time from investors in connection with a behavior investment plan. These entities will have a view into de-identified information for a wide range of individuals to analyze and learn what sorts of techniques, products, incentives, services etc., were well received by investors and worked to improve the relevant behavior.

Moreover, investors may voluntarily (i.e., with their permission) avail themselves to marketing or advertisements from product or service providers who have access to the de-identified information. For example, when the server 100 generates an investor report or encouragement message to an investor, the server 100 may associate a targeted or tailored message from an advertiser who has learned about the investor through the data collected by the server 100, but does not know the identity of the investor.

Further still, the data collected by the server 100 may be used to compute a behavior credit score for an investor that the investor can use, voluntarily, to prove to a prospective employer, insurer, dating service, social network, etc., that he/she is a good risk for insurance and/or has a healthy lifestyle, etc. Only the investor can authorize release of the behavior credit score to a third party.

Set forth below are examples of applications of the system and method described herein.

Example 1

Time Clock Technology Based Data Collection and Reporting Tools

The following is an example of a computer-based (but not necessarily server-based) implementation of a behavior investment plan using known and existing software and hardware.

Equipment and software used: Exaktime™ JobClocks (wand stations), outdoor protective cover if there is an outside wand station, green keytabs (wands), other color wands, Palm Pilot Zire™, JobClock Manager™ software, Microsoft Excel™. The Exaktime software interacts with wireless, portable, battery-powered time clocks that may be placed indoors or outdoors. Investors "clock in" at the different time clocks by swiping a wand at the center of the clock. Using infra-red technology, the Palm Pilot Zire™ collects information from the time clocks when a designated official holds the Palm Pilot device in a certain position near the time clock. The information collected is then transmitted to the JobClock Manager software by synchronizing the Palm Pilot device with the computer that operates the JobClock Manager software. The JobClock Manager software runs time reports for payroll purposes, but can also be configured so that one type of report, called an exception report, lists the clock, identification number or description of the wand swiped at the clock, and the time of the swipe.

Exaktime JobClock Technology to Capture Data for Use with the Self-Tracking and Encouragement System Step One. Using the set up information provided by Exaktime, assign a location name to each of the wand stations.

Walking, running routes or stair-climbing: In general, locations should be at the beginning, middle and end points of a physical activity route. Example, for a stair-climbing route, name wand stations "Top Floor" "Middle Floor" and "Lobby." The middle wand station is used to discourage fraud. It can be eliminated if there are structural or other barriers to fraud already. For example, a mall-walking route may only require two well-placed wand stations, named "Mall One" and "Mall Two," simply because it takes such a long time to park and walk to either wand station that it is unlikely investors would do so.

Fitness Center: When the activity takes place in one location, such as an on-site gym or fitness center, only one wand station bearing the name of the location is necessary.

Cafeterias: Name a wand station for each cashier location.

Health Promotion Activity: Name a wand station to be used for different health-promotion activities. This wand station can be used for periodic events, such as company-sponsored walks, weekly support group meetings, health fairs or other activities for which you want to reward attendance. This wand station will be identified by activity wands (see below).

Step Two. Using the information provided by Exaktime, assign an identification number or name or description to keytabs (wands).

Participant/Investor Identifications: Each participant or investor is a random HealthBux account number upon enrollment. Each wand tag is labeled with an investor's name, but in the JobClock Manager program the wand is assigned to the investor's account number. This wand is the investor's identification wand, which he or she will use to self-track his or her presence at the wand station locations.

Food Descriptions: If it is desired to use wand station to capture different kinds of food purchases, descriptions are associated with wands that inform the software program what the wand station is being used for at a particular time. For example, if is desired to track fruit and salad consumption at the company cafeteria, one wand is assigned the name "Fruit" in the JobClock Manager software and given a wand tag labeled "Fruit" as well. Different colors may be useful to distinguish these wands from the investors' identification wands. Assign another (different colored) wand the name "Salad" in the JobClock Manager software and give it a wand tag labeled the same. Attach both activity wands to the cafeteria wand station using a durable attachment device that is long enough for the wand to dangle from the wand station when not in use and then reach the wand station when needed. To indicate that an investor has purchased a salad, he/she swipes the Salad wand attached to the Cafeteria wand station and then swipes his/her identification wand. The software program will read: Wand Station Cafeteria—Salad at 12:42:03 pm, Mary at 12:42:05 pm and translate this to Mary purchased salad and earned HealthBux credits for doing so. (HealthBux is a health-specific term derived from the more general term BehaviorBux referred to above.)

Activity Descriptions: Activity description wands can be used to identify different activities tracked by the roaming Activity wand station. This allows for rewarding activities at any time and obtaining detailed reporting on the activities. If desired, a wand can be named for each event. Example: "Healthy Legs Road Race 2005" "Weight Watchers meeting on-site" "Lunch and Learn on Weight Maintenance During the Holidays." By doing this, it is possible to create detailed reports on attendance at specific events, but it is necessary to rename the wand for the next event. Alternatively, activities may be given categories. Example: "Physical activity group event" "group support meeting" "educational meeting."

HealthBux Credit: Wands can be used to identify different HealthBux values for different activities. If it is desired to award HealthBux credit for a particular event, investors can swipe the appropriate HealthBux value wand. For example, if is desired to provide an extra incentive for investors to attend an educational meeting, you would swipe the "educational meeting" wand, followed by the "HealthBux 20" wand before allowing all attendees to swipe their own identification wands. The HealthBux software program reads "educational meeting" at 9:00:00 am "HealthBux 20" at 9:00:02 am Account Number 24 at 9:00:06 am, 25 at 9:00:12 am etc. and interpret that data to show that Account Numbers 24 and 25 attended an educational meeting and earned 20 HealthBux credit for doing so.

End of Activity: Wands can be used to indicate the end of an activity. When an official swipes an "End of Activity" wand, the software program stops applying the description or HealthBux value previously swiped to any subsequent swipes. For example, a wand station located in the gym is usually used to indicate a regular workout worth 20 Health-Bux. A participant must swipe in, work out for 30 minutes or more, and swipe out. The company agrees to award 100 HealthBux for anyone who takes an Introduction to Yoga Stress Release class at the gym. At the gym wand station, an instructor swipes a "physical activity event" wand followed by a HealthBux value 100 wand, and then permits all class members to swipe their identification wands. After everyone has swiped in, the instructor swipes the End of Activity wand. Joe, Mary and Ed go to the yoga class and swipe their wands after the physical activity event wand and the HealthBux 100 wand, but before the End of Activity wand. Fred just does his normal workout and swipes his wand after the End of Activity wand has been swiped. The software program can differentiate the activities and HealthBux credit values for each of these individuals because the End of Activity wand tells it when to treat further swipes according to the regular set up for that wand station.

Winners of Challenges and Games: For games and challenges in which individuals will compete for prizes, the Roaming wand station can be used to designate winning Teams or individuals.

Teams

Example: Company Olympics features teams from Sales, Production and Finance departments. First place earns the Team 100 HealthBux, second 50, 3rd 10. Sales Team wins the Relay walk around the plant. An official swipes an "Olympics" wand at the start of the Olympics—this designates all the swipes that follow as Olympics events. Then, the official swipes the wand marked "Relay Walk." After Sales Team wins, official presents Team representative with the Red 1st place Wand (assigned value of 100 HealthBux) and representative swipes the Wand. The Sales Team HealthBux Account Statement will show 100 HealthBux earned for Relay Walk in the Company Olympics.

Individuals

Example: Company Olympics features a 10 k race. Three Roaming wand stations are swiped with an "Olympics" wand. At the start of the race, each wand station is swiped with a "10 k" wand. Then each wand station is swiped with Health-Bux 20 (value assigned just for participating in the 10 k). Participants run with their wands and swipe in at one of the Wand Stations as they finish. The System reads: Olympics 8:00 am, 10 k 8:30 am, HealthBux 20 8:31:00 am, Account Number 24 8:50:02 am, Account Number 25 8:55:04 am, Account Number 28 9:15:07 am. The HealthBux Account Statement for each individual might read Olympics 10 k-20 HealthBux Time: x minutes, y seconds.

Buddies or Group Support:

Wands can be used to identify when individuals are participating in an activity or food purchase together. This is very helpful for promoting a buddy system or for encouraging experienced investors to engage in activities with new investors or investors who have decreased participation. Example: participants can earn 5 extra HealthBux if they engage in a designated activity with another member of the program. The extra HealthBux will be awarded to both participants if the system sees both participants swipe at the same wand station within a 15 second time window. Example: experienced participants and novices can earn "Mentor" HealthBux every time they engage in an activity together. The system identifies certain wand numbers as belonging to Mentors and certain wand numbers as belonging to Novices. Each time a Mentor wand swipes a wand station within 15 seconds of a Novice, both members get extra HealthBux.

Step Three. Communicate program rules and base HealthBux values to investors and distribute wands.

Step Four. Collect data from wand stations using the hand-held Palm Zire™ device provided by Exaktime.

Step Five. Synchronize the Palm Zire™ device to the computer that has JobClock Manager installed on it.

Step Six. Open JobClock Manager and go to reports. Under reports, choose exception report, "print as excel document".

Step Seven. Name the exception report according to the dates of data collected and save. Example: Pilot program 91 to 9152005.

Step Eight. Open the Master ACE Model and locate the tab marked report.

Step Nine. Copy the exception report for the dates you want and paste it over whatever exception report is currently in the tab marked report. (Do this by clicking top left corner box of spreadsheet, then selecting edit, copy. On report tab, click top left corner box of spreadsheet and click paste.)

Step Ten. Go to the Report Output tab and select process report. This will cause the software program to calculate activities and HealthBux values for all participants using the most recent data pulled from the wand stations and all previous records.

Step Eleven. Go to the statistics tab of the Master ACE Model program. To view an individual's activities, select the activity bar at the top. To view an investor's HealthBux Account balance, select the HealthBux earned bar at the top.

Step Twelve. To email out HealthBux Account Statements for all investors, open the MasterPartcipantFile, Master ACE Model program, and Microsoft Outlook. Go to the statistics tab of the Master ACE Model program and make sure it shows the data to be sent out. Instead of the participant's name at the top, it will only have the account number. However, when the email macro is executed, the number will be replaced by the name. To test the email macro, add a blank row after the first entry on the MasterParticipantFile and change the first listing's email address to a particular email address. Go back to the Statistics page and select Tools, Macro, Macros. When the "email active participant" is displayed, select Run. The system will send the Account Statement for the first investor listed in the Master Participant File to the designated email address.

Example 2

HealthBux Investment Program FAQ Enrollment, Screening, Toolkit

What was it Like to Enroll in the HealthBux Investment Program?

To enroll in the HealthBux Investment Program, I went to www.aceideasconsulting.com/portal. It took about 15 minutes to complete and asked questions about my physical activity, food choices and things I do to get support for physical activity and healthy eating.

What was the screening like? It wasn't bad at all. I didn't have to fast and the fingerprick was quick and practically painless.

What did you have to do at the screening? First, I wrote my HIP Account Number on a screening report sheet. The screener measured my height and weighed me on the scale. Then the screener took my blood pressure. Finally, she gave me a fingerprick and ran a slide through a machine. The machine created a report that showed my glucose level, total cholesterol and HDL. The screener wrote all my information down on the screening report sheet with my number on it. It showed my height, weight, Body Mass Index, blood pressure, glucose level and total cholesterol.

How long did the screening take? It took about fifteen minutes. I read some materials and took a comprehension assessment while I waited.

So, what were your results? Well, since I'm a fictitious person, I'll tell you! They were:

High glucose level, high cholesterol level, BMI of 30, normal blood pressure.

What did the screener say about this? Well, we were around other people, so she didn't say much. In fact, there was a sign reminding everyone to talk softly and avoid commenting on their results. But she did point to the part of the report that explains the results and says I should get retested by my doctor for glucose and cholesterol. The report also shows that I am over the normal BMI and need to lose weight. She asked if I understood this recommendation and gave me her card if I have any questions.

What did you do with the screening report? I gave it to another screener for her to enter the data into the HealthBux Investment Program database next to my private Account Number. I received a HealthBux Opening Account Statement and a HealthBux Investment Kit.

What is the HealthBux Opening Account Statement? It is like a bank statement. It explains my Impact Factor and makes suggestions on how I can earn HealthBux.

What is the Impact Factor? ACE Ideas uses my Body Mass Index and age to determine my Impact Factor. That is like a handicap for a sport, and it enables everyone to compete fairly for HealthBux.

How can I calculate my Impact Factor? Everyone starts with an Impact Factor of 1. If you are 30 or older, you may add to the Impact Factor. For each decade, you add a 0.1. (30 to 39, add 0.1; 40 to 49, add 0.2, etc.) If you are overweight, obese or morbidly obese, you may add to the Impact Factor. For BMI of 26-29, add 0.2; for 30-35, add 0.4; for BMI of 36 or more, add 0.6.

What if I lose weight and go from obese to overweight? Will my Impact Factor go down? No. In order to encourage weight loss and recognize the importance of physical activity in maintaining weight loss, you will always keep the Impact Factor you receive at your first enrollment.

What are HealthBux? HealthBux represent units of health-promoting behavior. Each unit of health-promoting behavior is assigned a HealthBux value. No matter where the HealthBux program is offered, similar units of physical activity will have similar values. For example, the values of stair-climbing units are based on the energy expenditure and difficulty associated with stair-climbing. The value of walking a set walking route is based on the energy expenditure associated with walking that route. Values for physical activity units were refined and approved by Dr. Paul Vanderburgh, an expert in health and sport science. Values associated with engaging in health-promoting behaviors with buddies, participating in special events and screenings, and completing educational modules are developed based on the needs of the particular population and research associated with such behaviors and their impact on health and productivity.

Is there a real money value for HealthBux? No. The organization that sponsors the HealthBux Investment Program decides how many HealthBux must be earned in order to obtain incentives. This allows organizations maximum flexibility when designing the program.

How do I earn HealthBux? See the Rules for Investors document for 1) a list of health-promoting behavior units 2) their HealthBux values and 3) prizes for the current Session.

Why do overweight and obese investors get to multiply base HealthBux for physical activity units by an Impact Factor? Is this really fair? The formula for the Impact Factor was carefully constructed to take into account the additional energy expenditure (measured in calorie expenditure and oxygen consumption) required for overweight and obese investors to complete the physical activity units. This formula was refined and approved by Dr. Paul Vanderburgh, Chair of the Health and Sport Science Department of the University of Dayton, Ohio. Dr. Vanderburgh has considerable experience developing sport handicaps using objective evidence of energy expenditure.

Why do investors over age 30 get to multiply base HealthBux by an Impact Factor? Is this really fair? The formula for the Impact Factor was carefully constructed to take into account the impact of aging on the body's cardiovascular abilities. Dr. Vanderburgh's extensive research developing the "Flyer Handicap," which enables older and heavier runners to compete for prizes against younger, lighter runners of a 5K race, is the foundation of the calculation of the age component of the HealthBux Impact Factor.

What is the HealthBux Investment Kit?

The HealthBux Investment Kit contained a HealthBux pedometer, a HealthBux wand, and a keychain that has my Account Number and the Hotline phone number on it.

How Does the HealthBux Pedometer Work?

I clip the pedometer on my waistband or belt and attach the safety cord to my waistband or belt as well. To clear the pedometer, I press both silver buttons at once. Even though I clear the pedometer, it remembers how many steps I took each day of the week. In order to earn HealthBux, I have to upload the pedometer once a week.

Do You Wear the Pedometer at Work?

Yes. I wear it at work and to client meetings. Although my jacket covers it, if my client asks about it, I tell him or her about how my company is 100% committed to developing a workforce that is highly productive, physically active (as appropriate) and well nourished. Although the HealthBux Investment Program is voluntary, earning HealthBux helps me demonstrate that I "walk the walk" and really care about my company and fellow workers.

What is the HealthBux Hotline?

The HealthBux Hotline enables investors to earn HealthBux by visiting health-promoting locations, such as an offsite gym, park or weight loss program meeting. To earn HealthBux, I just call the Hotline from the landline phone at the location (1-800-640-2099) or my cellphone. I enter the last four digits of my Account number and follow the directions. If I call from my cellphone, I make sure I am wearing my pedometer so ACE Ideas can verify the activity through its random audit procedure.

The HealthBux Hotline is also a way that investors can earn HealthBux when they are prevented by injury or illness from engaging in physical activity. Those investors may earn HealthBux by calling the Hotline to plan and evaluate healthy choices for the day.

How Does the HealthBux Wand Work?

The HealthBux wand works with the HealthBux wand station to prove that I do a number of different health-promoting activities. It is very easy to use. I just swipe the wand to the center of the Wand Station and wait for 3 beeps. The 3 beeps proves that my choice has been counted.

Where are the Wand Stations?

There are two at Lenox mall, so I can earn HealthBux by walking to the mall and around the mall. (Atlanta only)

There are three in the stairwell, so I can earn HealthBux by climbing stairs during short breaks at work. (Atlanta only)

There is one near the reception desk, so I can earn Health-Bux by eating fruits and vegetables during the workday.

There is one in the gym, so I can earn HealthBux by working out at the on-site gym during the day. (Atlanta only)

Why Use the Wand and Wand Station when You Already Have the Pedometer?

Our company wants to promote physical activity and healthy eating and make wellness part of our culture. It also wants to encourage associates to take short, intense physical activity breaks and nourishing fruit/vegetable breaks during the day. Research shows that productivity increases a lot when individuals take short activity/nourishment breaks during working hours. By making it easy to earn HealthBux during the work day, physical activity and good nutrition become a visible, celebrated part of our work culture.

The wand and wand station also make it easy to track attendance at investment meetings and award HealthBux for special activities. Whenever there is an Investment Meeting, I bring my wand to make sure I earn HealthBux for attending.

How Else Does the HealthBux Investment Program Help Develop a Productive, Energized Workforce?

Whenever we earn HealthBux at work by using the wand and wand system, we can earn extra BuddyBux by swiping before or after another investor. This encourages investors to take activity and nourishment breaks together and encourage each other in their wellness efforts. We can also earn extra HealthBux by attending a Champion-sponsored event. We prove attendance by using our wand at one of the wand stations.

Is this a Weight Loss Program?

No, but active participation does promote weight loss. The goals of the program are to reward physical activity and proper nourishment, and to promote and celebrate healthy choices. However, investors may earn HealthBux by attending weight loss programs, completing weight loss education modules and planning and evaluating their food choices if desired. We have special weight maintenance challenges during the Holiday Season and we provide information about the impact of proper nourishment on productivity.

Why are Spouses Allowed to be Investors?

Healthy habits are hard to develop and maintain. It is easier to work on those habits with the support of the family. Spouses earn HealthBux by using the pedometer and the HealthBux Hotline. They can attend meetings by phone or in person. Celebrating their accomplishments shows how much our company cares about the well-being of associates and their families.

Example 3

Set forth below is an example of an instructional message that may be made available to investors as part of a health investment plan. This message informs the investors that work in a particular building how to achieve certain investment credit for engaging in different degrees of physical activity.

BASE HEALTHBUX VALUES

Stairs (tenants only) - take the stairs nearest the entrance to NBC (on 28) or next to the "Ambition" sign (on 23). Swipe your wand at each wand station you pass. They are located in the stairwell on 28, 23, and in the mailroom. There are no exits between 23 and the mailroom!

| 3 | $28^{th}$ Floor Down to $23^{rd}$ Floor |
| 5 | $23^{rd}$ Floor Up to $28^{th}$ Floor |
| 12 | $28^{th}$ Floor Down to $23^{rd}$ Floor Down to Mailroom (total of 20 floors) |
| 9 | $23^{rd}$ Floor Down to Mailroom (total of 15 floors) |
| 15 | Mailroom Up to $23^{rd}$ Floor (total of 15 floors) |
| 20 | Mailroom Up to $23^{rd}$ Floor Up to $28^{th}$ Floor (total of 20 floors) |

To enter the $23^{rd}$ or $28^{th}$ floor from the stairwell, enter the reentry code on the keypad.

| 10 (max. 3 fruits and 1 salad per day) | If you bring a salad or fruit to the reception desk at NBC, you can earn HealthBux. For a fruit, swipe the "fruit" wand first, then swipe your own wand. For a salad, swipe the "salad" wand first, then swipe your own wand. Only whole fruits (recognizable - no purees, smoothies jams etc.) and vegetables (salads or raw vegetables) may be credited.

| 20 | Gym (tenants only, no spouses) - your passcard for the building has been activated to allow you to use the building's gym. To earn HealthBux by visiting the gym, just swipe your wand at the wand station in the gym at the beginning and end of your workout. To earn HealthBux, you must stay in the gym for 30 minutes.

| 20 | Walk from Atlanta Plaza to Lenox Mall and Back - Swipe your wand at the mailroom wand station and walk to Lenox Mall. Swipe your wand at the Walking Company (wand station is in the basket of walking sticks at the entrance). Swipe your wand again at the mailroom upon your return.

| 10 | Mall Loop - Swipe your wand at the Walking Company and at

NikeWomen (wand station is attached to a sign at the entrance).

| 20 | Call in from Physical Activity Location (off-site gym, zoo, golf course, bike path, any place that requires you to move around). Call 1-800-640-2099 and enter the last three digits of your Account Number. Follow the directions.

Example 4

Set forth below is exemplary text of rules and information about presented to participants of a health investment program implemented according to the techniques of the present invention.

TopProfitsUSA, Inc. HealthBux™ Investment Program Join NOW or Re-Enroll for Session Two!

What is it?

The HealthBux™ Investment Program is like a frequent flier program or other affinity program. It is a FUN, innovative, hassle-free way to track your own investments in health and earn "Dividend!" points to purchase exciting merchandise through our online catalog.

Why do it?

By linking REWARDS to health-promoting BEHAVIORS, the Program supports a well-nourished, energized, productive workforce. If you want to INCREASE ENERGY, PRODUCTIVITY and FUN and SELECT REWARDS YOU LIKE, you should become a HealthBux™ Investor.

How Does it Work?

Investors use special data collection and reporting tools to PROVE participation in health-promoting BEHAVIORS, such as eating fruits and vegetables and taking activity breaks at work, wearing a pedometer, visiting health-promoting locations and participating in investment meetings. Units of health-promoting behavior are assigned a HealthBux™ value. Each week, investors receive a HealthBux™ Account Statement showing their HealthBux™ investments. Each month, investors who reach investment goals receive Dividend! points to purchase items in the online catalog. Participation in the HealthBux™ Investment Program is completely voluntary.

How Much Time Does it Take?

The Program is designed to take VERY LITTLE TIME. Program Champions George Washington and Abraham Lincoln are BUSY, focused leaders who understand that regular physical activity and proper nourishment are CRITICAL to their productivity. One of the reasons they chose this program is that it is uniquely suited to the needs of hard workers with tight schedules.

What about Investors with Health Limitations?

The HealthBux™ Investment Program is for everyone! Investors who are overweight, sedentary or facing other challenges identified in enrollment screenings receive an Impact Factor at the health screening. HealthBux™ investments linked to physical activity will be multiplied by the Impact Factor so everyone may compete fairly. (This is like getting a "handicap" in golf.) Investors who are unable to engage in any physical activity may earn HealthBux™ by completing other health promotion activities approved by ACE Ideas.

How do I Join or Rejoin for Session Two?

Enrollment is simple. Please see the attached page called INSTRUCTIONS FOR ENROLLING.

---

IMPORTANT UPCOMING EVENTS

Kick-off Meeting Hosted by George Washington and Abraham Lincoln
Friday, Mar. 24, 2006, 12:00-1:30 in the Training Room
Health Screenings: Thursday, Mar. 30, 2006 - 9:00-3:00
Sign-up for an appointment at www.xyz.com/portal
No Fasting Required; Allocate 30 minutes

---

HealthBux™ Investment Program

What do Investors do?

All Investors track their own investments in personal health using the HealthBux™ tools:

- ★ ☆ An uploadable pedometer
- ★ ☆ A wand and/or
- ★ ☆ The Hotline (1-800-640-2099)

Each week, they receive a HealthBux™ Account Statement that shows their activities and the HealthBux™ they invested.

If an Investor meets the investment goal of 1,000 or more HealthBux™ invested in a month, he or she will receive Dividend! points. All HealthBux™ have a dividend value, because they may be spent at the Casino Party and Silent Auction at the end of the Session.

What Happens at an Investment Meeting?

Investors meet for monthly Investment Meetings to celebrate their accomplishments, weigh-in (if desired), and learn how and why to make further investments in health. Each month is "hosted" by a HealthBux™ Investment Champion.

---

Investment Meeting Schedule and Topics for Session Two

| | | |
|---|---|---|
| ★ ☆ | April | Productivity - Full Engagement Part I. "Beat the Boss" Challenge |
| ★ ☆ | May: | Productivity - Full Engagement Part II. |
| ★ ☆ | June: | Feeding the Brain - Productivity and Food |
| ★ ☆ | July: | Health and Wealth |
| ★ ☆ | August: | Happiness and Satisfaction - two scientific perspectives |
| ★ ☆ | September: | Casino Party and Silent Auction hosted by George Washington |

---

What About Privacy?

The HealthBux™ Investment Program is operated by ACE Ideas, LLC. We take privacy of health information very seriously. The enrollment form that contains an Investor's contact information is maintained in strictest confidence. Each enrolled Investor is assigned an account number by ACE Ideas, LLC. The key that links the member's name to the account number is kept securely by ACE Ideas, LLC, in accordance with federal guidelines for protection of highly sensitive health information.

What Does the Program Cost?

The Program is FREE for Session Two. Investors pay a refundable deposit for the HealthBux™ pedometer ($30) and wand (employees only) ($12), which will be returned at the end of Session Two.

The screening is free for new Investors and is $10 for Investors who participated in Session One.

---

INSTRUCTIONS FOR ENROLLING
In the
HealthBux ™ Investment Program - Session Two

| | |
|---|---|
| Step 1 | Go to www.xyzconsulting.com/portal to sign up for a quick health screening. No fasting is required. If this is your first time at this site, you must Register and create an account: 1. Click REGISTER 2. Fill in the required fields. For User Name pick a name you'd like to be called for purposes of corresponding on the portal. You must designate an e-mail address. 3. Click "New Item" to see available times for Health Screenings - select an appointment time. You will receive an e-mail confirmation of your appointment time. |
| Step 2 | At this same site, click on the Enrollment Form link. Password is healthbux Complete the Enrollment Form (it takes 15 minutes). |
| Step 3 | Attend the Kickoff Meeting: March 24$^{th}$ from 12:00-1:30 The Kickoff Meeting will be hosted by George Washington and Abraham Lincoln. |
| Step 4 | Attend your health screening at your designated appointment time. Get your health screening results. Pick up your Investor Toolkit. |

---

To participate in the HealthBux™ Investment Program Session Two, you must enroll at this time NOTE to Investors from Session One Your enrollment is not automatic You must actively enroll again for Session Two

| Investment Opportunities | | | |
|---|---|---|---|
| | HealthBux ™ Values × IF | BuddyBux ™ Values | Directions |
| ACTIVITIES Applicable HealthBux ™ Values are multiplied by Impact Factor (IF) | | | |
| Fresh Whole Fruit, Salad or Raw Vegetable at Work Food or receipt showing work - day purchase. | 10 (5/day max) | +2 per swipe | Wand at Reception desk. Must swipe wand before or after Buddy to receive +2 |
| HealthBux ™ Event sponsored by a Champion -- attend | | 50 | Swipe wand immediately after Champion |
| Health - promoting location | 20 | | Call the Hotline from its landline phone to track visit |
| Investment Education Module - complete one | 50 | | |
| Mall: Atlanta Plaza to Lenox Mall and Back Swipe wand: mailroom station when leave and when return; at the Walking Company immediately upon arrival | 20 × IF | +6 (2 per swipe if you go with a Buddy) | |
| Mall Loop Swipe wand: Walking Company-->Nike Women-->Walking Company | 10 × IF | +2 per swipe | |
| Monthly Investment Meeting -- attend | 50 | | Bring wand to meeting |
| Monthly Investment Meeting - weigh-in | 50 | | Bring wand to meeting |
| Monthly Investment Meeting - bring another investor | | 50 | Bring wand to meeting |
| On-site Gym - 30 minute minimum workout | 20 | +2 per swipe | Swipe gym's wand station before & after workout |
| Participate in a community walk or run with another investor | | 100 | Call Hotline and email proof of event (photo or signed flyer) to ACE Ideas |
| Stairs: 28$^{th}$ Floor Down to 23$^{rd}$ Floor | 3 × IF | +2 per swipe | Must swipe wand before or after Buddy |
| Stairs: 23$^{rd}$ Floor Up to 28$^{th}$ Floor | 5 × IF | +2 per swipe | |
| Stairs: 23$^{rd}$ Floor Down to Mailroom (15 floors) | 9 × IF | +2 per swipe | Swipe wand at 23$^{rd}$ floor wand station |
| Stairs: 28$^{th}$ Floor Down to 23$^{rd}$ Floor Down to Mailroom (20 floors) | 12 × IF | +2 per swipe | |
| Stairs: Mailroom Up to 23$^{rd}$ Floor (15 floors) | 15 × IF | +2 per swipe | |
| Stairs: Mailroom Up to 23$^{rd}$ Floor Up to 28$^{th}$ Floor (20 floors) | 20 × IF | | |
| Session Two Evaluation (Complete in September, 2006) | 100 | | |
| PEDOMETER | | | |
| 1,000-4,999 steps in a day | 15 × IF | | Upload pedometer once a week using dedicated computer |
| 5,000-9,999 steps in a day | 30 × IF | | |
| 10,000-14,999 steps in a day | 60 × IF | | |
| 15,000+ steps in a day | 80 × IF | | |

TOTAL Health Bux ™ earned for a month = HealthBux ™ Values + BuddyBux ™ Values
To encourage you to participate with another Investor, prizes will also be awarded for BuddyBux ™ earned.
HealthBux ™ Hotline is: 1-800-640-2099

| Investment Opportunities for Spouses | | | |
|---|---|---|---|
| | HealthBux ™ Values | BuddyBux ™ Values | Directions |
| ACTIVITIES | | | |
| Health-promoting location - visit | 20 | | Call the Hotline from its landline phone to track visit |
| Monthly Investment Meeting -- attend | 50 | | Bring wand to meeting |
| Monthly Investment Meeting - weigh-in | 50 | | Bring wand to meeting |
| Monthly Investment Meeting - bring another investor | | 50 | Bring wand to meeting |
| Investment Education Module - complete one | 50 | | |
| Participate in a community walk or run with another Investor | | 100 | Call Hotline and email proof of event (photo or signed flyer) to ACE Ideas |
| Session Two Evaluation (complete in September, 2006) | 100 HB × IF (Impact Factor | | |
| PEDOMETER | | | |
| 1,000-4,999 steps in a day | 15 × IF | | Upload pedometer once a week using dedicated computer |
| 5,000-9,999 steps in a day | 30 × IF | | |
| 10,000-14,999 steps in a day | 60 × IF | | |
| 15,000+ steps in a day | 80 × IF | | |

TOTAL HealthBux ™ earned for a month = HealthBux ™ Values + BuddyBux ™ Values
To encourage you to participate with another Investor, prizes will also be awarded for BuddyBux ™ earned.
HealthBux ™ Hotline is: 1-800-640-2099

| Investment Opportunities for Investors Unable to Engage in Physical Activity | | | |
|---|---|---|---|
| ACTIVITIES | HealthBux ™ Values | BuddyBux ™ Values | Directions |
| Fresh Whole Fruit, Salad or Raw Vegetable at Work Food or receipt showing work-day purchase. | 10 (5/day max) | +2 per swipe | Wand at Reception desk. Must swipe wand before or after Buddy to get BuddyBux |
| Health-promoting location - visit Doctor's office, support group, massage, weight loss program meeting | 20 | | Call the Hotline from its landline phone to track visit |
| Hotline - Call to plan your healthy choices for the day | 20 | | Call Hotline |
| Hotline - Call to evaluate your healthy choices for the day | 20 | | |
| Interview a fellow investor; write a paragraph on his or her investment strategies and successes | | 50 | Call Hotline and e-mail paragraph to ACE Ideas |
| Investment Education Module - complete one | 50 | | |
| Monthly Investment Meeting -- attend | 50 | | |
| Monthly Investment Meeting - weigh-in | 50 | | |
| Monthly Investment Meeting - bring another investor | | 50 | |
| Session Two Evaluation (complete in September, 2006) | 100 | | |

TOTAL HealthBux ™ earned for a month = HealthBux ™ Values + BuddyBux ™ Values
To encourage you to participate with another Investor, prizes will also be awarded for BuddyBux ™ earned.
HealthBux ™ Hotline is: 1-800-640-2099

Awards for Session Two

Monthly Prizes
The top two Investors who invest the most HealthBux™ (including BuddyBux™) each receive 10,000 Dividend! points (limited to once per Session).
The Investor who invests the most BuddyBux™ receives 10,000 Dividend! points (limited to once per Session.)
Each Investor who invests over 1,500 HealthBux™ for the month receives 6000 Dividend points
Each Investor who invests over 1,000 HealthBux™ for the month receives 3000 Dividend points
Golden Ticket Days
Golden Ticket Days will occur during the month but will be unannounced.
Any investor who invest HealthBux™ in any amount on these days will receive a Golden Ticket.
Tickets will have differing values and may be redeemed at the Monthly Investment Meeting or at the Casino and Silent Auction.
Grand Prizes for Session Two
At the end of September, a Grand Prize will be awarded to each of the following:
   Investor with the highest Account Balance (total Health-Bux™ and BuddyBux™)
   Investor with the most consistent and diversified investments (healthy activities)
   Investor with the most BuddyBux™
The Grand Prize for each winner is $300 and $300 donated by the Company to the charity chosen by each winner.

In view of the foregoing detailed description of preferred embodiments of the present invention, it readily will be understood by those persons skilled in the art that the present invention is susceptible to broad utility and application. While various aspects have been described in the context of screen shots, additional aspects, features, and methodologies of the present invention will be readily discernable therefrom. Many embodiments and adaptations of the present invention other than those herein described, as well as many variations, modifications, and equivalent arrangements and methodologies, will be apparent from or reasonably suggested by the present invention and the foregoing description thereof, without departing from the substance or scope of the present invention. Furthermore, any sequence(s) and/or temporal order of steps of various processes described and claimed herein are those considered to be the best mode contemplated for carrying out the present invention. It should also be understood that, although steps of various processes may be shown and described as being in a preferred sequence or temporal order, the steps of any such processes are not limited to being carried out in any particular sequence or order, absent a specific indication of such to achieve a particular intended result. In most cases, the steps of such processes may be carried out in various different sequences and orders, while still falling within the scope of the present inventions. In addition, some steps may be carried out simultaneously. Accordingly, while the present invention has been described herein in detail in relation to preferred embodiments, it is to be understood that this disclosure is only illustrative and exemplary of the present invention and is made merely for purposes of providing a full and enabling disclosure of the invention.

What is claimed is:
1. A method comprising:
   a. at a computing device, storing information to enroll a plurality of individuals such that the individuals become participants in a comprehensive healthy behavior reinforcement plan established by a sponsor entity, wherein the comprehensive healthy behavior reinforcement plan is designed to encourage one or more desired healthy behaviors for the participants, and assigning participants to one of a plurality of groups;
   b. at the computing device, storing baseline data or measurements related to the one or more desired healthy behaviors or its impact on the one or more desired healthy behaviors for each participant;
   c. at the computing device, computing one or more handicapping factors for a participant based on the baseline data or measurements for that participant that represents that participant's effort needed to complete at least a particular healthy behavior activity;

d. generating at a plurality of activity data capture devices activity data that represents participant activities that are relevant to the one or more desired healthy behaviors for each participant;

e. at the computing device, computing for each participant an adjusted point value resulting from performance of the particular activity based on the handicapping factor that represents that participant's effort needed to complete the particular activity, and computing group performance measurement data comprising an aggregate point value for a group of participants based on a sum of adjusted point values for participants in the corresponding group from the performance of the particular activity;

f. presenting the performance measurement data to the corresponding participant and presenting the group performance measurement data to participants of the corresponding group and to participants of other groups;

g. comparing the aggregate point values associated with performance of the particular activity for which the groups compete against each other; and h. allocating awards to participants based on the comparing.

2. The method of claim 1, and further comprising receiving one or more of: data indicating a measure of physical activity of a participant related to the one or more desired healthy behaviors; data from a point of transaction system that indicates proof of purchase of items or services associated with the one or more desired healthy behaviors; data indicating presence of a participant at a facility relevant to the one or more desired healthy behaviors; data from a body-attachable activity monitor device on a participant that indicates a measure of an activity related to the one or more desired healthy behaviors.

3. The method of claim 2, wherein the comprehensive healthy behavior reinforcement plan is designed to improve the health of the participants, and wherein receiving comprises receiving activity data related to participant activities that are related to health improvement.

4. The method of claim 3, wherein receiving comprises receiving from equipment deployed in or near a facility where the participants frequent physical activity data that detect identity, time and location information of the participants in or near the facility, and further comprising analyzing the physical activity data to assign a measurement value thereto.

5. The method of claim 3, wherein receiving comprises receiving activity data from point of transaction equipment that enables participants to voluntarily identify themselves and register an event related to health improvement of the participant.

6. The method of claim 2, and further comprising receiving the data through one or a combination of a wide area wireless and/or wired network and local area wireless and/or wired network.

7. The method of claim 1, wherein (e) computing further comprises computing values that indicate degree of improvement or achievement of the one or more desired healthy behaviors by a participant.

8. The method of claim 7, and further comprising storing for each participant data representing points awarded to a participant based on the degree of improvement or achievement of the one or more desired healthy behaviors by the participant, and the participants redeeming their points at a supplier of goods or services.

9. The method of claim 1, wherein (a) storing, (b) storing and (f) presenting are performed in compliance with laws and/or regulations governing privacy and security for health related information.

10. The method of claim 9, and further comprising receiving from a participant an authorization to permit otherwise unauthorized entities to have access to a participant's baseline healthy behavior information and/or performance measurement data, and storing the authorization received from the participant, and wherein said receiving and storing of the authorization is performed in compliance with said laws and/or regulations governing privacy an security for health related information.

11. The method of claim 1, and further comprising computing one or more incentives for the participants that are designed to encourage the participants to achieve the one or more desired healthy behaviors of the comprehensive healthy behavior reinforcement plan, and determining whether a participant has achieved the one more incentives based on the participant's performance measurement data adjusted for the participant's one or more handicapping factors.

12. The method of claim 1, wherein the sponsor entity is an employer and participants are employees of said employer, and further comprising receiving one or more of: information related to the work environment provided by said employer; impact of the work environment and effect on the one or more desired healthy behaviors; and information related to potential economic impact to the employer of the one or more desired healthy behaviors.

13. The method of claim 1, wherein (g) presenting comprises presenting performance measurement data concurrent with advertisement content from one or more advertisers that supply goods and/or services that are related to and supportive of the desired one or more behaviors.

14. The method of claim 1, and further comprising computing an economic impact of improvement of healthy behaviors of the participants; and computing data identifying and/or describing parameters for the one or more desired healthy behaviors based on said economic impact.

15. The method of claim 1, and further comprising storing data representing audio, video and/or text encouragement messages from one or more individuals associated with the sponsor entity at the time the comprehensive healthy behavior reinforcement plan is established, and delivering at a later time the encouragement messages to participants.

16. The method of claim 1, and further comprising generating for each individual that becomes a participant, unique de-identification information that is used to track a participant's progress in the comprehensive healthy behavior reinforcement plan, wherein said de-identification information does not contain any information that directly reveals an identity of the participant, wherein (a) storing through (f) presenting are performed with respect to de-identification information for each individual that becomes a participant.

17. The method of claim 1, wherein (b) storing comprises storing baseline behavior information which includes information describing physical and behavioral characteristics of an environment where a participant is on a daily basis, and further comprising receiving activity data representing a participant's activity and healthy behavior choices, and wherein (f) presenting comprises presenting one or more messages to a participant to reinforce the participant's daily activity and healthy behavior choices.

18. The method of claim 1, wherein (b) storing baseline data or measurements comprises storing biometric screening data related to the health of a participant, and wherein (c)

computing comprises computing a handicapping factor for a participant further based on an age of the participant.

19. The method of claim 1, and further comprising computing point values for a member of a group based on his/her engaging in a healthy behavior activity with another participant in his/her group.

20. A comprehensive behavior reinforcement system, comprising:
   a. one or more computing devices that receive, store and process data;
   b. a plurality of activity data capture devices connected to the one or more computing devices by one or more: of a wired or wireless wide area and wired or wireless local area network;
   c. wherein the one or more computing devices perform functions of:
      i. storing information to enroll a plurality of individuals such that the individuals become participants in a comprehensive healthy behavior reinforcement plan established by a sponsor entity, wherein the comprehensive behavior reinforcement plan is designed to encourage one or more desired healthy behaviors for the participants, and assigning participants to one of a plurality of groups;
      ii. storing baseline data or measurements related to the one or more desired healthy behaviors or its impact on the one or more desired healthy behaviors for each participant;
      iii. computing one or more handicapping factors for a participant based on the baseline data or measurements for that participant that represents that participant's effort needed to complete at least a particular healthy behavior activity;
      iv. collecting the activity data from the plurality of activity data capture devices;
      v. computing for each participant an adjusted point value resulting from performance of the particular activity based on the handicapping factor that represents that participant's effort needed to complete the particular activity, and computing group performance measurement data comprising an aggregate point value for a group of participants based on the a sum of adjusted point values for participants in the corresponding group from the performance of the particular activity; comparing the aggregate point values associated with performance of the particular activity for which the groups compete against each other to allocate awards to the participants based on the comparison.

21. The system of claim 20, wherein the one or more computing devices are configured to compute one or more incentives for the participants that are designed to encourage the participants to achieve the one or more desired healthy behaviors of the comprehensive healthy behavior reinforcement plan, and to determine whether a participant has achieved the one more incentives based on the participant's performance measurement data adjusted for the participant's one or more handicapping factors.

22. The system of claim 20, wherein the plurality of activity data capture devices are configured to receive one or more of data indicating a measure of physical activity of a participant related to the one or more desired behaviors; data from a point of transaction system that indicates proof of purchase of items or services associated with the one or more desired behaviors; data indicating presence of a participant at a facility relevant to the one or more desired behaviors; data from a body-attachable activity monitor device on a participant that indicates a measure of an activity related to the one or more desired behaviors.

23. The system of claim 20, wherein the plurality of activity data capture devices are configured to receive from equipment deployed in or near a facility where the participants frequent physical activity data that detect identity, time and location information of the participants in or near the facility, and wherein the one or more computing devices are configured to analyze the physical activity data to assign a measurement value thereto.

24. The system of claim 20, wherein one or more activity data capture devices are configured to receive activity data from point of transaction equipment that enables participants to voluntarily identify themselves and register an event related to health improvement of the participant.

25. The system of claim 20, wherein the one or more computing devices are configured to store data representing audio, video and/or text encouragement messages from one or more individuals associated with the sponsor entity at the time the comprehensive behavior reinforcement plan is established, and to present at a later time the encouragement messages to participants.

26. The system of claim 20, wherein the one or more computing devices are configured to generate for each individual that becomes a participant, unique de-identification information that is used to track a participant's progress in the comprehensive healthy behavior reinforcement plan, wherein said de-identification information does not contain any information that directly reveals an identity of the participant.

27. The system of claim 20, wherein the one or more computing devices are configured to store baseline behavior information which includes information describing physical and behavioral characteristics of an environment where a participant is on a daily basis, and wherein one or more activity data capture devices are configured to receive activity data representing a participant's activity and healthy behavior choices in said environment, and the one or more computing devices are configured to presenting one or more messages to a participant to reinforce the participant's daily activity and healthy behavior choices in their environment.

28. The system of claim 20, wherein the one or more computing devices are configured to compute point values for a member of a group based on his/her engaging in a healthy behavior activity with another participant in his/her group.

* * * * *